US012343376B2

(12) United States Patent
Kroemer et al.

(10) Patent No.: US 12,343,376 B2
(45) Date of Patent: *Jul. 1, 2025

(54) METHODS FOR INHIBITING DIAZEPAM BINDING PROTEIN

(71) Applicants: INSTITUT NATIONAL DE LA SANTÉ ET DE LA RECHERCHE MÉDICALE, Paris (FR); ASSISTANCE PUBLIQUE-HÔPITAUX DE PARIS (APHP), Paris (FR); UNIVERSITÉ PARIS CITÉ, Paris (FR); SORBONNE UNIVERSITÉ, Paris (FR)

(72) Inventors: Guido Kroemer, Paris (FR); José Manuel Bravo San Pedro, Paris (FR)

(73) Assignees: INSTITUT NATIONAL DE LA SANTÉ ET DE LA RECHERCHE MÉDICALE, Paris (FR); ASSISTANCE PUBLIQUE-HÔPITAUX DE PARIS (APHP), Paris (FR); UNIVERSITÉ PARIS CITÉ, Paris (FR); SORBONNE UNIVERSITÉ, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 18/444,102

(22) Filed: Feb. 16, 2024

(65) Prior Publication Data

US 2024/0245750 A1 Jul. 25, 2024

Related U.S. Application Data

(63) Continuation of application No. 17/935,261, filed on Sep. 26, 2022, now Pat. No. 11,905,330, which is a continuation of application No. 16/648,744, filed as application No. PCT/EP2018/075286 on Sep. 19, 2018.

(30) Foreign Application Priority Data

Sep. 20, 2017 (EP) .................................. 173062293

(51) Int. Cl.
| | |
|---|---|
| *A61K 39/395* | (2006.01) |
| *A61K 38/17* | (2006.01) |
| *A61K 39/00* | (2006.01) |
| *A61K 39/39* | (2006.01) |
| *A61P 3/04* | (2006.01) |
| *C07K 16/18* | (2006.01) |
| *C07K 16/28* | (2006.01) |
| *G01N 33/68* | (2006.01) |

(52) U.S. Cl.
CPC .......... *A61K 38/17* (2013.01); *A61K 39/0005* (2013.01); *A61K 39/39* (2013.01); *A61P 3/04* (2018.01); *C07K 16/18* (2013.01); *C07K 16/286* (2013.01); *G01N 33/68* (2013.01); *A61K 2039/505* (2013.01); *A61K 2039/545* (2013.01); *C07K 2317/21* (2013.01); *C07K 2317/24* (2013.01)

(58) Field of Classification Search
None
See application file for complete search history.

(56) References Cited

U.S. PATENT DOCUMENTS

2016/0250249 A1 9/2016 Kroemer

FOREIGN PATENT DOCUMENTS

WO 2001025436 A2 4/2001

OTHER PUBLICATIONS

Paschos et al. (2009). Hippokratia 13(1):9-19.*
Abcam web site (retrieved from https://www.abcam.com/dbi-antibody-ab16871.html on Jan. 25, 2023, 2 pages) (Year: 2023).
Alho, H., et al., "Diazepam Binding Inhibitor (DBI) processing: Immunohistochemical studies in the rat brain" Neurochem Res 15, 209-216 (1990). https://doi.org/10.1007/BF00972211.
Alho, H., et al., "Diazepam binding inhibitor gene expression: location in brain and peripheral tissues of rat" Proc Natl Acad Sci U S A. Sep. 1988;85(18):7018-22. doi: 10.1073/pnas.85.18.7018.

(Continued)

*Primary Examiner* — Christine J Saoud
*Assistant Examiner* — Jon M Lockard
(74) *Attorney, Agent, or Firm* — Greenberg Traurig, LLP

(57) ABSTRACT

Autophagy is typically activated by starvation, allowing cells and organisms to mobilize their energy reserves. It is known that pharmacological modulation of autophagy represents a therapeutic potential. Here the inventors report that a protein that is released from cells in an unconventional, autophagy-dependent manner, namely, diazepam binding inhibitor (DBI), regulates autophagy. In particular, the inventors demonstrate that DBI inhibits autophagy and that the supply of recombinant DBI to mice enhanced glycolysis, enhanced lipogenesis, and inhibited fatty acid oxidation. The inventors show that neutralisation of DBI by a monoclonal antibody and an active immunization by means of an immunogenic DBI derivative eliciting autoantibodies induce autophagy and lead to metabolic changes that increase starvation-induced weight loss, reduce food intake upon refeeding, and reduce weight gain in response to hypercaloric diets. Accordingly, the present invention relates to methods and pharmaceutical compositions for modulating autophagy based on the modulation of the activity or expression of DBI.

17 Claims, 7 Drawing Sheets

Figure 2C:
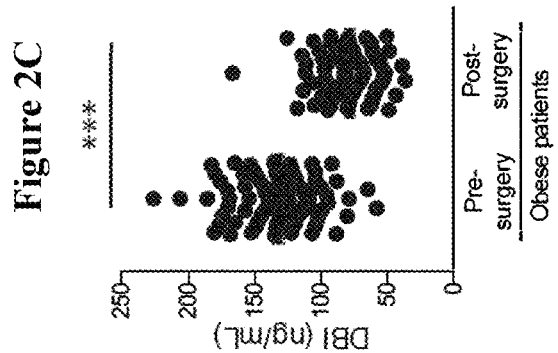

Specification includes a Sequence Listing.

(56) References Cited

OTHER PUBLICATIONS

Barbaccia, M.L., et al., "DBI (Diazepam Binding Inhibitor): The precursor of a family of endogenous modulators of GABA A receptor function. History, perspectives, and clinical implications" Neurochem Res 15, 161-168 (1990). https://doi.org/10.1007/BF00972206.

Costa, E. & Guidotti, A., "Diazepam binding inhibitor (DBI): a peptide with multiple biological actions" Life Sci. 1991;49(5):325-44. doi: 10.1016/0024-3205(91)90440-m.

Egan, D. F., et al., "Phosphorylation of ULK1 (hATG1) by AMP-activated protein kinase connects energy sensing to mitophagy" Science. Jan. 28, 2011;331(6016):456-61. doi: 10.1126/science.1196371.

Elle, I. C., et al., "Tissue- and paralogue-specific functions of acyl-CoA-binding proteins in lipid metabolism in Caenorhabditis elegans" Biochem J. Jul. 15, 2011;437(2):231-41. doi: 10.1042/BJ20102099.

Fernandez, A. F., et al., "Autophagy couteracts weight gain, lipotoxicity and pancreatic β-cell death upon hypercaloric pro-diabetic regimens" Cell Death Dis. Aug. 3, 2017;8(8):e2970. doi: 10.1038/cddis.2017.373.

Ferrarese, C., et al., "Acute noise stress in rats increases the levels of diazepam binding inhibitor (DBI) in hippocampus and adrenal gland" Psychopharmacology 103, 339-342 (1991). https://doi.org/10.1007/BF02244287.

Ferrero, P., et al., "Study of an octadecaneuropeptide derived from diazepam binding inhibitor (DBI): biological activity and presence in rat brain" Proc Natl Acad Sci U S A. Feb. 1986;83(3):827-31. doi: 10.1073/pnas.83.3.827.

Keane, J., et al., "Mechanosensory inputs influence Caenorhabditis elegans pharyngeal activity via ivermectin sensitivity genes" Genetics. May 2003;164(1):153-62. doi: 10.1093/genetics/164.1.153.

Knudsen, J. et al., "The function of acyl-CoA-binding protein (ACBP)/diazepam binding inhibitor (DBI)" Mol Cell Biochem, Jun. 1993, vol. 123, pp. 129-138.

Lesouhaitier, O., et al., "Localization of diazepam-binding inhibitor-related peptides and peripheral type benzodiazepine receptors in the frog adrenal gland" Cell Tissue Res 283, 403-412 (1996). https://doi.org/10.1007/s004410050551.

Melendez, A., et al., "Autophagy genes are essential for dauer development and life-span extension in C. elegans" Science. Sep. 5, 2003;301(5638):1387-91. doi: 10.1126/science.1087782.

Palmisano, N. J., et al., "Detection of Autophagy in Caenorhabditis elegans Using GFP::LGG-1 as an Autophagy Marker" Cold Spring Harb Protoc. Jan. 4, 2016;2016(1):pdb.prot086496. doi: 10.1101/pdb.prot086496.

Snyder, M.J., et al., "Evidence for a diazepam-binding inhibitor (DBI) benzodiazepine receptor-like mechanism in ecdysteroidogenesis by the insect prothoracic gland" Cell and Tissue Res, vol. 294, pp. 161-168, May 1998.

Bek, S., et al., "Compromised epidermal barrier stimulates Harderian gland activity and hypertrophy in ACBP-/- mice" J Lipid Res. Sep. 2015;56(9):1738-46. doi: 10.1194/jlr.M060780.

Berkovich, A., et al., "A natural processing product of rat diazepam binding inhibitor, triakontatetraneuropeptide (diazepam binding inhibitor 17-50) contains an alpha-helix, which allows discrimination between benzodiazepine binding site subtypes" Mol Pharmacol. Feb. 1990;37(2):164-72.

Bloksgaard, M., et al., "Acyl-CoA binding protein and epidermal barrier function" Biochim Biophys Acta. Mar. 2014;1841(3):369-76. doi: 10.1016/j.bbalip.2013.09.013.

Bloksgaard, M., et al., "The acyl-CoA binding protein is required for normal epidermal barrier function in mice" J Lipid Res. Oct. 2012;53(10):2162-2174. doi: 10.1194/jlr.M029553.

Bormann, J., et al., "Electrophysiological characterization of diazepam binding inhibitor (DBI) on GABA A receptors" Neuropharmacology. Dec. 1991;30(12B):1387-9. doi: 10.1016/s0028-3908(11)80006-7.

Bouyakdan, K., et al., "A novel role for central ACBP/DBI as a regulator of long-chain fatty acid metabolism in astrocytes" J Neurochem. Apr. 2015;133(2):253-65. doi: 10.1111/jnc.13035.

Budry, L., et al., "DBI/ACBP loss-of-function does not affect anxiety-like behaviour but reduces anxiolytic responses to diazepam in mice" Behav Brain Res. Oct. 15, 2016;313:201-207. doi: 10.1016/j.bbr.2016.06.052.

Christain, C. A., et al., "Endogenous positive allosteric modulation of GABA(A) receptors by diazepam binding inhibitor" Neuron. Jun. 19, 2013;78(6):1063-74. doi: 10.1016/j.neuron.2013.04.026. Epub May 30, 2013.

Chye, M., "*Arabidopsis* cDNA Encoding a Membrane-Associated Protein with an acyl-CoA Binding Domain", Plant Molecular Biology, Mar. 1998, vol. 38, pp. 827-838.

Conti et al: "Reduced fasting plasma levels of diazepam-binding inhibitor in adolescents with anorexia nervosa : Plasma Dbi in Anorexia Nervosa", International Journal of Eating Disorders, vol. 46, No. 6, pp. 626-629, Apr. 29, 2013.

Conti, E., et al., Reduced fasting plasma levels of diazepam-binding inhibitor in adolescents with anorexia nervosa. Int J Eat Disord. Sep. 2013;46(6):626-9. doi: 10.1002/eat.22129.

Czaja, M. J., "Function of Autophagy in Nonalcoholic Fatty Liver Disease", Dig Dis Sci. May 2016;61(5):1304-13. doi: 10.1007/s10620-015-4025-x.

Do Rego et al: "Pharmacological Characterization of the Receptor Mediating the Anorexigenic Action of the Octadecaneuropeptide: Evidence for an Endozepinergic Tone Regulating Food Intake", Neuropsychopharmacology, vol. 32, No. 7, pp. 1641-1648, Jul. 1, 2007.

Dupont, N., et al., "Autophagy-based unconventional secretory pathway for extracellular delivery of IL-1β" EMBO J. Nov. 8, 2011;30(23):4701-11. doi: 10.1038/emboj.2011.398.

Duran, J. M., et al., "Unconventional secretion of Acb1 is mediated by autophagosomes" J Cell Biol. Feb. 22, 2010;188(4):527-36. doi: 10.1083/jcb.200911154.

Fan, W., et al., "Cloning and functions of the HBxAg-binding protein XBP1" Mol Med Rep. Feb. 2013;7(2):618-22. doi: 10.3892/mmr.2012.1232.

Farzampour, U. J., et al., Endozepines. Adv Pharmacol. 2015;72:147-64. doi: 10.1016/bs.apha.2014.10.005. Epub Dec. 4, 2014. PMID: 25600369.

Feddersen, S. and Faergeman, N. J., "Perturbation of Intracellular acyl-CoA Metabolism Induces the Unfolded Protein Response Pathway and Autophagy in *Saccharomyces cerevisiae*", Abstracts Posters session7: Lysosomal Lipid Metabolism (PO 108-114), Chemistry and Physics of Lipids, 154S (2008) S61-S63; PO 109, 1 page.

Gallego, S. F., "Quantitative lipidomics reveals age-dependent perturbations of whole-body lipid metabolism in ACBP deficient mice" Biochim Biophys Acta Mol Cell Biol Lipids. Feb. 2017;1862(2):145-155. doi: 10.1016/j.bbalip.2016.10.012.

Gandolfo, P., et al., "The stimulatory effect of the octadecaneuropeptide (ODN) on cytosolic Ca2+ in rat astrocytes is not mediated through classical benzodiazepine receptors" Eur J Pharmacol. Mar. 19, 1997;322(2-3):275-81. doi: 10.1016/s0014-2999(97)00012-5.

Gandolfo, P., et al., "The triakontatetraneuropeptide TTN increases [CA2+]i in rat astrocytes through activation of peripheral-type benzodiazepine receptors" Glia. Aug. 2001;35(2):90-100. doi: 10.1002/glia.1074.

Gray, P. W., et al., "Cloning and expression of cDNA for human diazepam binding inhibitor, a natural ligand of an allosteric regulatory site of the gamma-aminobutyric acid type A receptor" Proc Natl Acad Sci U S A. Oct. 1986;83(19):7547-51. doi: 10.1073/pnas.83.19.7547.

Guillebaud, F., et al., "Glial Endozepines Inhibit Feeding-Related Autonomic Functions by Acting at the Brainstem Level" Front Neurosci. May 30, 2017;11:308. doi: 10.3389/fnins.2017.00308.

Kawaguchi et al: "Subcellular localization of acyl-CoA binding protein inAspergillus oryzaeis regulated by autophagy machinery", Biochemical and Biophysical Research Communications, vol. 480, No. 1, pp. 8-12, Oct. 7, 2016.

Kim, K. H., et al., "Autophagy—a key player in cellular and body metabolism" Nat Rev Endocrinol. Jun. 2014;10(6):322-37. doi: 10.1038/nrendo.2014.35.

(56) References Cited

OTHER PUBLICATIONS

Landrock, D., et al., "Acyl-CoA binding protein gene ablation induces pre-implantation embryonic lethality in mice. Lipids" Jul. 2010;45(7):567-80. doi: 10.1007/s11745-010-3437-9.

Lanfray et al: "Gliotransmission and Brain Glucose Sensing: Critical Role of Endozepines", Diabetes, vol. 62, No. 3, pp. 801-810, Nov. 16, 2012.

Lanfray, D., et al., "Gliotransmission and brain glucose sensing: critical role of endozepines" Diabetes. Mar. 2013;62(3):801-10. doi: 10.2337/db11-0785.

Langaa, S., et al., "Mice with targeted disruption of the acyl-CoA binding protein display attenuated urine concentrating ability and diminished renal aquaporin-3 abundance" Am J Physiol Renal Physiol. Apr. 15, 2012;302(8):F1034-44. doi: 10.1152/ajprenal.00371.2011.

Leprince, J., et al., "Synthesis, conformational analysis and biological activity of cyclic analogs of the octadecaneuropeptide ODN" Design of a potent endozepine antagonist. Eur J Biochem. Dec. 2001;268(23):6045-57. doi: 10.1046/j.0014-2956.2001.02533.x.

Levine, B. et al., "Autophagy in immunity and inflammation" Nature. Jan. 20, 2011;469(7330):323-35. doi: 10.1038/nature09782.

Li, Y., et al., "Diazepam-binding inhibitor mediates feedback regulation of pancreatic secretion and postprandial release of cholecystokinin" J Clin Invest. Feb. 2000;105(3):351-9. doi: 10.1172/JCI7204.

Marino, G., et al., "Regulation of autophagy by cytosolic acetyl-coenzyme A" Mol Cell. Mar. 6, 2014;53(5):710-25. doi: 10.1016/j.molcel.2014.01.016.

Matsuda et al: "Effect of the diazepam-binding inhibitor-derived peptide, octadecaneuropeptide, on food intake in goldfish", Neuroscience, vol. 150, No. 2, pp. 425-432, Dec. 5, 2007.

Mizushima, N., "Autophagy fights disease through cellular self-digestion" Nature. Feb. 28, 2008;451(7182):1069-75. doi: 10.1038/nature06639.

Mizushima, N., et al., "In vivo analysis of autophagy in response to nutrient starvation using transgenic mice expressing a fluorescent autophagosome marker" Mol Biol Cell. Mar. 2004;15(3):1101-11. doi: 10.1091/mbc.e03-09-0704.

Neess, D., e tal., "ACBP—a PPAR and SREBP modulated housekeeping gene" Mol Cell Biochem. Mar. 2006;284(1-2):149-57. doi: 10.1007/s11010-005-9039-9. Epub Jan. 13, 2006. Erratum in: Mol Cell Biochem. May 2007;299(1-2):1-3.

Neess, D., et al., "Delayed hepatic adaptation to weaning in ACBP-/- mice is caused by disruption of the epidermal barrier" Cell Rep. Dec. 12, 2013;5(5):1403-12. doi: 10.1016/j.celrep.2013.11.010.

Neess, D., et al., Disruption of the acyl-CoA-binding protein gene delays hepatic adaptation to metabolic changes at weaning. J Biol Chem. Feb. 4, 2011;286(5):3460-72. doi: 10.1074/jbc.M110.161109.

Neess, D., et al., "Long-chain acyl-CoA esters in metabolism and signaling: Role of acyl-CoA binding proteins" Prog Lipid Res. Jul. 2015;59:1-25. doi: 10.1016/j.plipres.2015.04.001.

Neess, D., et al., "Long-chain acyl-CoA Esters in Metabolism and Signaling: Role of acyl-CoA Binding Proteins", Progress in Lipid Research, Apr. 2015, vol. 59, pp. 1-25.

Papadopoulos, V., et al. "Diazepam binding inhibitor and its processing products stimulate mitochondrial steroid biosynthesis via an interaction with mitochondrial benzodiazepine receptors" Endocrinology. Sep. 1991;129(3):1481-8. doi: 10.1210/endo-129-3-1481.

Patte, C., et al., "The endozepine ODN stimulates polyphosphoinositide metabolism in rat astrocytes" FEBS Lett. Apr. 3, 1995;362(2):106-10. doi: 10.1016/0014-5793(95)00209-r.

Ponpuak, M., et al., "Secretory autophagy" Curr Opin Cell Biol. Aug. 2015;35:106-16. doi: 10.1016/j.ceb.2015.04.016. Epub May 17, 2015.

Semernao, L., et al., "Targeting VEGF-A with a vaccine decreases inflammation and joint destruction in experimental arthritis" Angiogenesis. Jan. 2016;19(1):39-52. doi: 10.1007/s10456-015-9487-0.

Siejka et al: "Reduced plasma level of diazepam-binding inhibitor (DBI) in patients with morbid obesity", Endocrine, vol. 49, No. 3, pp. 859-562, Jan. 6, 2015.

Sinha, Rohit A., et al., "Caffeine stimulates hepatic lipid metabolism by the autophagy-lysosomal pathway in mice" Hepatology. Apr. 2014;59(4):1366-80. doi: 10.1002/hep.26667.

Tiller, Karhtyn E. & Tessier, Peter M., "Advances in Antibody Design", Annu Rev Biomed Eng. 2015;17:191-216. doi: 10.1146/annurev-bioeng-071114-040733, Epub Aug. 14, 2015.

Yang, L., et al., "Defective hepatic autophagy in obesity promotes ER stress and causes insulin resistance" Cell Metab. Jun. 9, 2010;11(6):467-78. doi: 10.1016/j.cmet.2010.04.005.

Zhang, M., et al., "Unconventional secretion, unconventional solutions" Science. May 3, 2013;340(6132):559-61. doi: 10.1126/science.

* cited by examiner

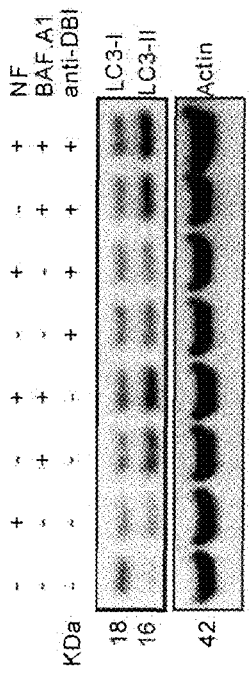
Figure 1A
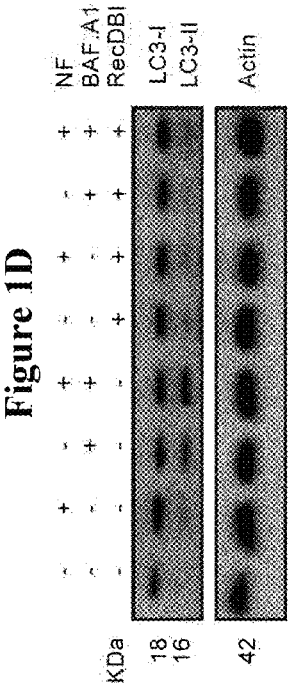
Figure 1C
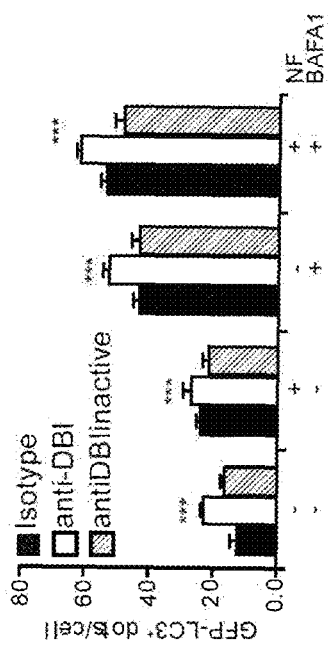
Figure 1E
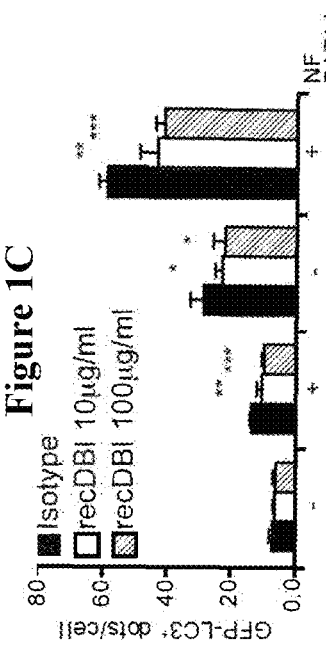
Figure 1F
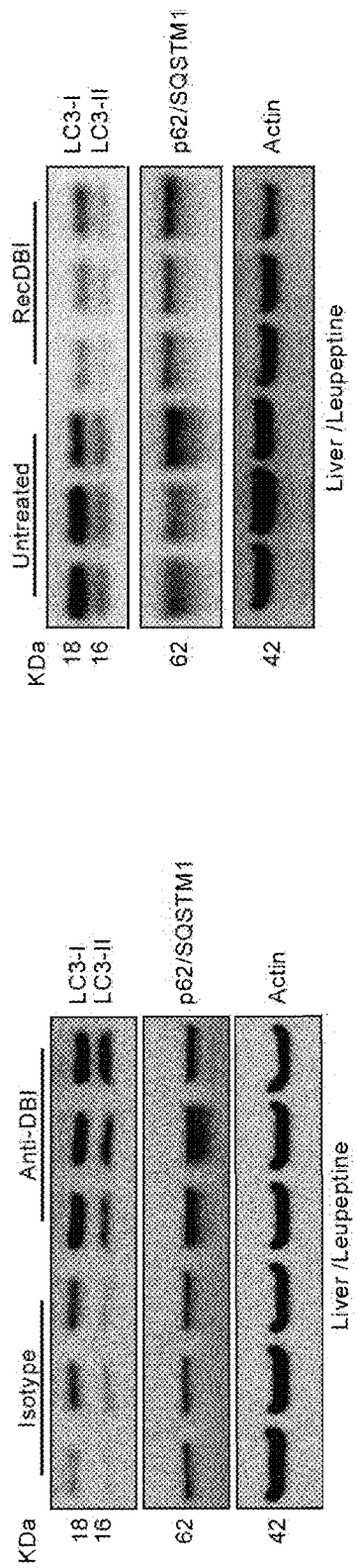
Figure 1B
Figure 1D

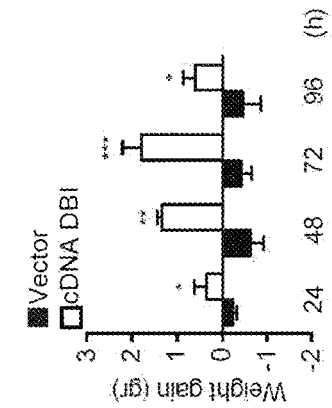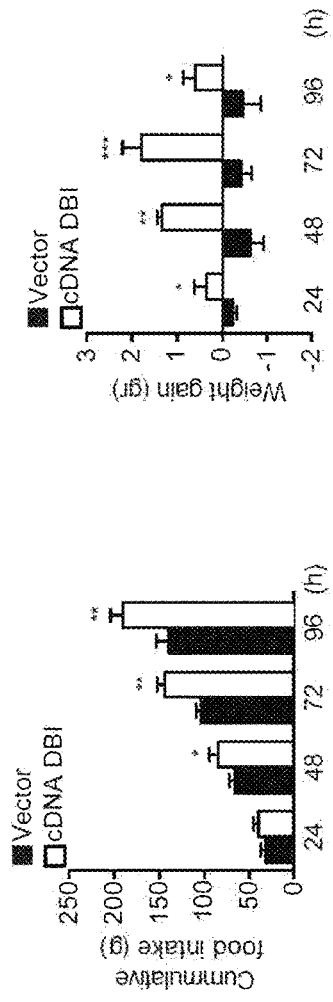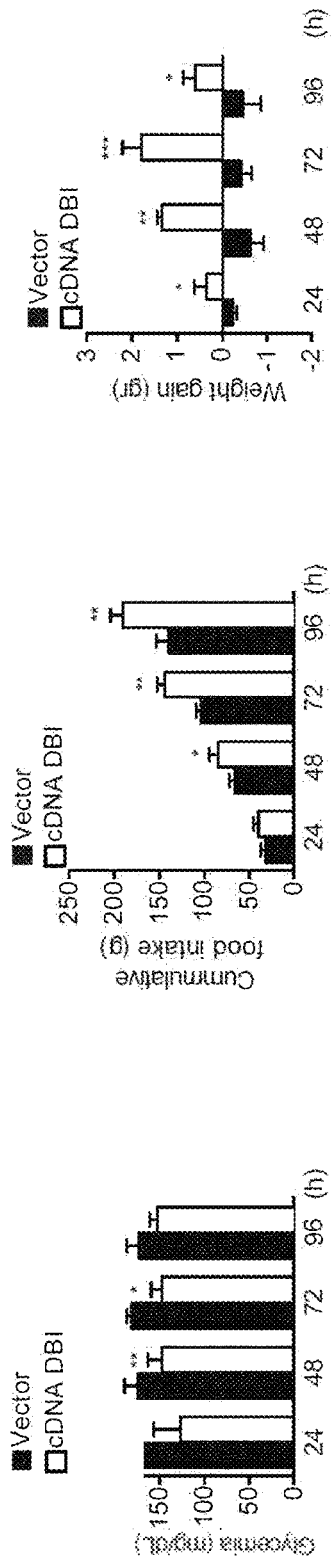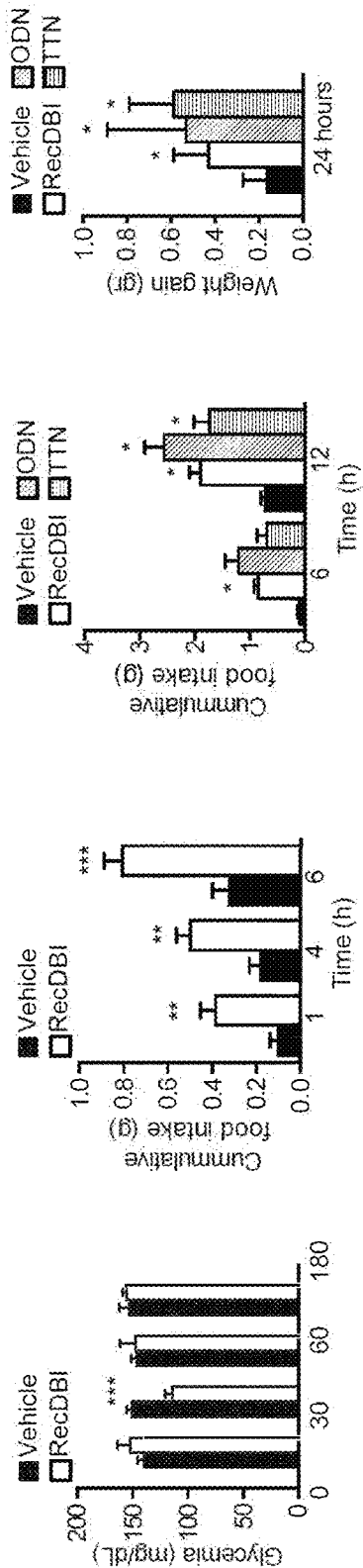
Figure 3A, Figure 3B, Figure 3C, Figure 3D, Figure 3E, Figure 3F, Figure 3G

```
                         SEQUENCE LISTING

Sequence total quantity: 2
SEQ ID NO: 1             moltype = AA    length = 87
FEATURE                  Location/Qualifiers
source                   1..87
                         mol_type = protein
                         organism = Homo sapiens
SEQUENCE: 1
MSQAEFEKAA EEVRHLKTKP SDEEMLFIYG HYKQATVGDI NTERPGMLDF TGKAKWDAWN    60
ELKGTSKEDA MKAYINKVEE LKKKYGI                                       87

SEQ ID NO: 2             moltype = DNA   length = 634
FEATURE                  Location/Qualifiers
source                   1..634
                         mol_type = genomic DNA
                         organism = Homo sapiens
SEQUENCE: 2
gctcgcccga gcagggttgg ggcgagtgga ccgcgcctct aaaggcgctt gccagtgcaa    60
tctgggcgat cgcttcctgg tcctcgcctc ctccgctgtc tccctggagt tcttgcaagt   120
cggccaggat gtctcaggct gagtttgaga aagctgcaga ggaggttagg caccttaaga   180
ccaagccatc ggatgaggag atgctgttca tctatggcca ctacaaacaa gcaactgtgg   240
gcgacataaa tacagaacgg cccgggatgt tggacttcac gggcaaggcc aagtgggatg   300
cctggaatga gctgaaaggg acttccaagg aagatgccat gaaagcttac atcaacaaag   360
tagaagagct aaagaaaaaa tacgggatat gagagactgg atttggttac tgtgccatgt   420
gtttatccta aactgagaca atgccttgtt tttttctaat accgtggatg gtgggaattc   480
gggaaaataa ccagttaaac cagctactca aggctgctca ccatacggct ctaacagatt   540
aggggctaaa acgattactg actttccttg agtagttttt atctgaaatc aattaaaagt   600
gtatttgtta ctttaaataa ctttaaaaaa aaaa                              634
```

METHODS FOR INHIBITING DIAZEPAM BINDING PROTEIN

CROSS-REFERENCE

This application is a continuation of U.S. patent application Ser. No. 17/935,261, filed Sep. 26, 2022, issued as U.S. Pat. No. 11,905,330 on Feb. 20, 2024, which is a continuation of U.S. patent application Ser. No. 16/648,744, filed Mar. 19, 2020, which is a National Stage Entry of International Application No. PCT/EP2018/075286, filed Sep. 19, 2018, which claims priority to EP Application No. 173062293.0, filed Sep. 20, 2017, all of which are herein incorporated by reference in their entirety

SEQUENCE LISTING

This application contains a Sequence Listing which has been submitted electronically in XML format, which is hereby incorporated by reference in its entirety. Said XML copy, created on Jan. 9, 2024 is named 206008-701303-SL and is 3,266 bytes in size.

FIELD OF THE INVENTION

The present invention relates to methods and pharmaceutical compositions for modulating autophagy.

BACKGROUND OF THE INVENTION

Autophagy ("self-eating") constitutes one of the most spectacular, though subtly regulated phenomena in cell biology and plays a key role in the maintenance of cellular and organismal homeostasis by facilitating the turnover of cytoplasmic structures and allowing cells to adapt to changing and stressful conditions including nutrient deprivation (1, 2). The cellular secretion of several leaderless proteins (which can only be released through an unconventional pathway bypassing Golgi) is strongly associated with autophagy (3-7). One such protein is a phylogenetically ancient factor known as diazepam binding protein (DBI) or acyl coenzyme A (CoA)-binding protein (ACBP) (3, 4). Human or mouse DBI is a small protein of 87 amino acids (10 kDa) that has two totally distinct functions, namely as ACBP within cells (where it binds to long-chain acyl CoA molecules) and as DBI outside cells (where the entire protein or its cleavage products, triacontatetraneuropeptide [TTN, residues 17-50] and octadecaneuroptide [ODN, residues 33-50], can interact with the benzodiazepine binding site of the gamma-aminobutyric acid type A receptor, $GABA_AR$, and modulate its activity as a GTP protein-coupled receptor, GPCR) (8-10). DBI and its proteolytic fragments also bind to the peripheral-type benzodiazepine receptor (PBR) (11-13), and a still unidentified GPCR (ODN-GPCR) (14-17). However, the role of DBI secretion in the feedback regulation of autophagy has never been investigated.

SUMMARY OF THE INVENTION

The present invention relates to methods and pharmaceutical compositions for modulating autophagy. In particular, the present invention is defined by the claims.

DETAILED DESCRIPTION OF THE INVENTION

Autophagy is typically activated by starvation, allowing cells and organisms to mobilize their energy reserves. Here the inventors report that a protein that is released from cells in an unconventional, autophagy-dependent manner, namely, diazepam binding inhibitor (DBI), also known as acyl coenzyme A-binding protein (ACBP), regulates autophagy at three levels. First, autophagy causes DBI secretion, depleting this pro-autophagic factor from the cell (autocrine regulation). Second, autophagy causes DBI accumulation in the extracellular space, allowing DBI to act on other cells to inhibit autophagy (paracrine regulation). Third, circulating DBI stimulates feeding behavior, hence removing the primary cause of autophagy induction (endocrine regulation). In humans, plasma DBI levels increase in obesity. Extra supply of recombinant DBI to mice enhanced glycolysis, enhanced lipogenesis, and inhibited fatty acid oxidation. The inventors also designed three strategies to neutralize DBI, namely, by inducible whole-body knockout, passive immunization, and active immunization by means of an immunogenic DBI derivative eliciting autoantibodies. These strategies favor metabolic changes that increase starvation-induced weight loss and reduce food intake upon refeeding.

General Definitions

As used herein, the term "subject", "individual," or "patient" is used interchangeably and refers to any subject for whom diagnosis, treatment, or therapy is desired, particularly humans. Other subjects may include cattle, dogs, cats, guinea pigs, rabbits, rats, mice, horses, and the like. In some preferred embodiments the subject is a human.

The term "autophagy" refers to macroautophagy, unless stated otherwise, is the catabolic process involving the degradation of a cell's own components; such as, long lived proteins, protein aggregates, cellular organelles, cell membranes, organelle membranes, and other cellular components. The mechanism of autophagy may include: (i) the formation of a membrane around a targeted region of the cell, separating the contents from the rest of the cytoplasm, (ii) the fusion of the resultant vesicle with a lysosome and the subsequent degradation of the vesicle contents. The term autophagy may also refer to one of the mechanisms by which a starving cell re-allocates nutrients from unnecessary processes to more essential processes. Also, for example, autophagy may inhibit the progression of some diseases and play a protective role against infection by intracellular pathogens. Acute, intermittent or continuous stimulation of autophagy can delay aging and aging-related diseases including arteriosclerosis, cardiac insufficiency, cancer and neurodegeneration. Stimulation of autophagy can also reduce high-fat or high-sugar diet or high-salt induced weight gain, obesity, metabolic syndrome, hypertension and diabetes.

As used herein, the term "body mass index" has its general meaning in the art and refers to refers to the ratio which is calculated as body weight per height in meter squared ($kg/m^2$). The BMI provides a simple means of assessing how much an individual's body weight departs from what is normal or desirable for a person of his or her height. Common definitions of BMI categories are as follows: starvation: BMI—less than 15 $kg/m^2$; underweight—BMI less than 18.5 $kg/m^2$; ideal—BMI from 18.5 to 25 $kg/m^2$; overweight—BMI from 25 to 30 $kg/m^2$; obese—BMI from 30 to 40 $kg/m^2$; morbidly obese—BMI greater than 40 $kg/m^2$. While simple, the BMI method of characterizing the body weight property of a person is not always correct. For example, the BMI does not take into account factors such as frame size, muscularity or varying proportions of e.g. bone, cartilage, and water weight among individuals. Thus, the accuracy of BMI in relation to actual levels of body fat mass may be distorted by such factors as fitness level, muscle mass, bone structure, gender, and ethnicity. Also, people with short stature and old people tend to have lower BMI values. It is considered, however, that the skilled person, e.g. a physician, will be able to take these factors into account when making the BMI assessment of any given individual.

As used herein, the term "cancer" has its general meaning in the art and includes, but is not limited to, solid tumors and blood borne tumors. The term cancer includes diseases of the skin, tissues, organs, bone, cartilage, blood and vessels. The term "cancer" further encompasses both primary and metastatic cancers. Examples of cancers that may treated by methods and compositions of the invention include, but are not limited to, cancer cells from the bladder, blood, bone, bone marrow, brain, breast, colon, esophagus, gastrointestine, gum, head, kidney, liver, lung, nasopharynx, neck, ovary, prostate, skin, stomach, testis, tongue, or uterus. In addition, the cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous; adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; and roblastoma, malignant; Sertoli cell carcinoma; leydig cell tumor, malignant; lipid cell tumor, malignant; paraganglioma, malignant; extra-mammary paraganglioma, malignant; pheochromocytoma; glomangiosarcoma; malignant melanoma; amelanotic melanoma; superficial spreading melanoma; malig melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; Hodgkin's disease; Hodgkin's lymphoma; paragranuloma; malignant lymphoma, small lymphocytic; malignant lymphoma, large cell, diffuse; malignant lymphoma, follicular; mycosis fungoides; other specified non-Hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia.

The terms "polypeptide" and "protein", are used interchangeably and refer to a polymeric form of amino acids of any length, which can include coded and non-coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous signal sequences, with or without N-terminal methionine residues; immunologically tagged proteins; and the like.

As used herein, the term "DBI" has its general meaning in the art and refers to the diazepam binding inhibitor, acyl-CoA binding protein encoding by the DBI gene (Gene ID: 1622). The term is also known as EP; ACBP; ACBD1; and CCK-RP. An exemplary human amino acid sequence is represented by the NCNI reference sequence NP_001073331.1 (SEQ ID NO:1) (acyl-CoA-binding protein isoform 1). An exemplary human nucleic acid sequence is represented by the NCNI reference sequence NM_001079862.2 (SEQ ID NO:2) (acyl-CoA-binding protein isoform 1).

```
                                            SEQ ID NO: 1
MSQAEFEKAA EEVRHLKTKP SDEEMLFIYG HYKQATVGDI

NTERPGMLDF TGKAKWDAWN ELKGTSKEDA MKAYINKVEE

LKKKYGI

SEQ ID NO: 2
GCTCGCCCGA GCAGGGTTGG GGCGAGTGGA CCGCGCCTCT

AAAGGCGCTT GCCAGTGCAA TCTGGGCGAT CGCTTCCTGG

TCCTCGCCTC CTCCGCTGTC TCCCTGGAGT TCTTGCAAGT

CGGCCAGGAT GTCTCAGGCT GAGTTTGAGA AAGCTGCAGA

GGAGGTTAGG CACCTTAAGA CCAAGCCATC GGATGAGGAG

ATGCTGTTCA TCTATGGCCA CTACAAACAA GCAACTGTGG
```

```
                               -continued
GCGACATAAA TACAGAACGG CCCGGGATGT TGGACTTCAC

GGGCAAGGCC AAGTGGGATG CCTGGAATGA GCTGAAAGGG

ACTTCCAAGG AAGATGCCAT GAAAGCTTAC ATCAACAAAG

TAGAAGAGCT AAAGAAAAAA TACGGGATAT GAGAGACTGG

ATTTGGTTAC TGTGCCATGT GTTTATCCTA AACTGAGACA

ATGCCTTGTT TTTTTCTAAT ACCGTGGATG GTGGGAATTC

GGGAAAATAA CCAGTTAAAC CAGCTACTCA AGGCTGCTCA

CCATACGGCT CTAACAGATT AGGGGCTAAA ACGATTACTG

ACTTTCCTTG AGTAGTTTTT ATCTGAAATC AATTAAAAGT

GTATTTGTTA CTTTAAATAA CTTTAAAAAA AAAA
```

As used herein, the term "DBI activity" refers to any biological activity of DIB that includes among others: inhibition of autophagy, induction of hypoglycaemia, stimulation of food intake, stimulation of weight gain, reduction of fatty acid oxidation, upregulation of glucose transporter, upregulation of PPARG, stimulation of glucose uptake, stimulation of glycolysis or stimulation of lipogenesis.

As used herein, the term "treatment" or "treat" refer to both prophylactic or preventive treatment as well as curative or disease modifying treatment, including treatment of patient at risk of contracting the disease or suspected to have contracted the disease as well as patients who are ill or have been diagnosed as suffering from a disease or medical condition, and includes suppression of clinical relapse. The treatment may be administered to a subject having a medical disorder or who ultimately may acquire the disorder, in order to prevent, cure, delay the onset of, reduce the severity of, or ameliorate one or more symptoms of a disorder or recurring disorder, or in order to prolong the survival of a subject beyond that expected in the absence of such treatment. By "therapeutic regimen" is meant the pattern of treatment of an illness, e.g., the pattern of dosing used during therapy. A therapeutic regimen may include an induction regimen and a maintenance regimen. The phrase "induction regimen" or "induction period" refers to a therapeutic regimen (or the portion of a therapeutic regimen) that is used for the initial treatment of a disease. The general goal of an induction regimen is to provide a high level of drug to a patient during the initial period of a treatment regimen. An induction regimen may employ (in part or in whole) a "loading regimen", which may include administering a greater dose of the drug than a physician would employ during a maintenance regimen, administering a drug more frequently than a physician would administer the drug during a maintenance regimen, or both. The phrase "maintenance regimen" or "maintenance period" refers to a therapeutic regimen (or the portion of a therapeutic regimen) that is used for the maintenance of a patient during treatment of an illness, e.g., to keep the patient in remission for long periods of time (months or years). A maintenance regimen may employ continuous therapy (e.g., administering a drug at a regular intervals, e.g., weekly, monthly, yearly, etc.) or intermittent therapy (e.g., interrupted treatment, intermittent treatment, treatment at relapse, or treatment upon achievement of a particular predetermined criteria [e.g., disease manifestation, etc.]).

By a "therapeutically effective amount" is meant a sufficient amount of the agent of the present invention for reaching a therapeutic effect. It will be understood, however, that the total daily usage of the compounds and compositions of the present invention will be decided by the attending physician within the scope of sound medical judgment. The specific therapeutically effective dose level for any particular subject will depend upon a variety of factors including the disorder being treated and the severity of the disorder; activity of the specific compound employed; the specific composition employed, the age, body weight, general health, sex and diet of the subject; the time of administration, route of administration, and rate of excretion of the specific compound employed; the duration of the treatment; drugs used in combination or coincidental with the specific compound employed; and like factors well known in the medical arts. For example, it is well within the skill of the art to start doses of the compound at levels lower than those required to achieve the desired therapeutic effect and to gradually increase the dosage until the desired effect is achieved. However, the daily dosage of the products may be varied over a wide range from 0.01 to 4,000 mg per adult per day. Typically, the compositions contain 0.01, 0.05, 0.1, 0.5, 1.0, 2.5, 5.0, 10.0, 15.0, 25.0, 50.0, 100, 250, 500 and 1000 mg of the active ingredient for the symptomatic adjustment of the dosage to the subject to be treated. A medicament typically contains from about 0.01 mg to about 1000 mg of the active ingredient. An effective amount of the drug is ordinarily supplied at a dosage level from 0.0002 mg/kg to about 50 mg/kg of body weight per day, especially from about 0.001 mg/kg to 10 mg/kg of body weight per day.

Methods of Inhibiting Autophagy:

Accordingly, the first object of the present invention relates to a method of inhibiting autophagy in a subject in need thereof comprising administering to the subject a therapeutically effective amount of an agent that promotes the activity or expression of DBI.

In some embodiments, the method of inhibiting autophagy according to the invention is particularly suitable for stimulating appetite and consequently weight gain. In particular, the method of the present invention is also particularly suitable for promoting glucose uptake and lipogenesis. Accordingly, the method of the present invention is particularly suitable for the treatment of various diseases as described herein after.

Accordingly, in some embodiments, the subject is underweight. As herein, the term "underweight" refers to a subject having a body mass index of below 18.5.

Underweight may be due to several causes, such as rapid metabolism, poor/inadequate diet or starvation (malnutrition), malabsorption due to defective intestinal function, endocrine disturbances e.g. type I diabetes, psychological problems (such as anorexia nervosa, body dysmorphic disorder, stress and anxiety) and weight loss, due to chronic illnesses and ageing. While in general the underlying cause of the underweight will have to be treated per se, the underweight too may be a health hazard, and as such have to be treated in itself. Indeed, persons suffering from underweight generally have poor physical stamina, a weakened immune system, as well as being at higher risk of developing diseases such as osteoporosis, heart disease and vascular disease. Additionally, in the female sex, underweight can lead to delayed sexual development, retarded amenorrhoea or complications during pregnancy.

In some embodiments, the subject suffers from a wasting disorder. As used herein, the term "wasting disorder" has its general meaning in the art and includes but is not limited to anorexia cachexia, anorexia of the aged, anorexia nervosa, cachexia associated with cancer, cachexia associated with AIDS, cachexia associated with heart failure, cachexia associated with cystic fibrosis, cachexia associated with rheumatoid arthritis, cachexia associated with kidney disease, cachexia associated with chronic obstructive pulmonary disease (COPD), cachexia associated with ALS, cachexia associated with renal failure or cachexia associated, and other disorders associated with aberrant appetite, fat mass, energy balance, and/or involuntary weight loss.

In some embodiments, the subject suffers from "cachexia". As used herein, the term "cachexia" is used for a condition of physical wasting with loss of body fat and muscle mass. Generally, cachexia may be associated with and due to conditions such as cancer, required immunodeficiency syndrome (AIDS), cardiac diseases, infectious diseases, shock, burn, endotoxinemia, organ inflammation, surgery, diabetes, collagen diseases, radiotherapy, and chemotherapy. In many of these diseases, cachexia may significantly contribute to morbidity or mortality. Another particular group of individuals that are susceptible to developing a cachectic state are those individuals that have undergone a gastrectomy, such as may be practiced on gastric cancer and ulcer patients.

In some embodiments, the subject suffers from anorexia. As used herein, the term "anorexia" has its general meaning in the art and refers to any eating disorder characterized by markedly reduced appetite or total aversion to food. In some embodiments, the subject suffers from anorexia nervosa. In general, subjects suffering from anorexia nervosa have a BMI of less than 17.5 kg/m$^2$.

Accordingly, the present invention is drawn to methods of treating a patient exhibiting one or more wasting disorders such as anorexia cachexia, anorexia of the aged, anorexia nervosa, cachexia associated with cancer, cachexia associated with AIDS, cachexia associated with heart failure, cachexia associated with cystic fibrosis, cachexia associated with rheumatoid arthritis, cachexia associated with kidney disease, cachexia associated with COPD, cachexia associated with ALS, cachexia associated with renal failure or cachexia associated, or hip fracture, and in reducing the mortality and morbidity of critically ill patients, comprising administering to said patient in need of such treatment a therapeutically effective of an agent that promotes the activity or expression of DBI.

In some embodiments, the subject suffers from a disease selected from the group consisting of cancer diseases, neurodegenerative diseases, cardiovascular diseases, infectious diseases, auto-immune diseases and/or inflammatory diseases.

In some embodiments, the subject suffers from a cancer. In particular, autophagy seems to be indispensable for tumor progression, providing the tumours with building blocks and energy for its increased metabolic requirements. The modulation of the tumours' metabolic environment by the administration of Agent that promotes the activity or expression of DBI alone or in combination with chemotherapeutic drugs may lead to a suppression of basal and starvation-induced autophagy, thus sensitizing tumour cells to the death. Accordingly, the Agent that promotes the activity or expression of DBI of the present invention would be suitable for the treatment of advanced cancer. In some embodiments, the cancer is an autophagy competent cancer. As used herein the term "autophagy competent cancer" denotes a cancer wherein autophagy could occur. In some embodiments, an ATG5 or ATG7 deficiency is not detected. In the context of the invention, the term "ATG5 or ATG7 deficiency" denotes that the tumor cells of the subject or a part thereof have an ATG5 or ATG7 dysfunction, a low or a null expression of ATG5 or ATG7 gene. Said deficiency may typically result from a mutation in ATG5 or ATG7 gene so that the pre-ARNm is degraded through the NMD (non sense mediated decay) system. Said deficiency may also typically result from a mutation so that the protein is misfolded and degraded through the proteasome. Said deficiency may also result from a loss of function mutation leading to a dysfunction of the protein. Said deficiency may also result from an epigenetic control of gene expression (e.g. methylation) so that the gene is less expressed in the cells of the subject. Said deficiency may also result from a repression of the ATG5 or ATG7 gene induce by a particular signalling pathway. Said deficiency may also result from a mutation in a nucleotide sequence that control the expression of ATG5 or ATG7 gene.

In some embodiments, the subject suffers from a neurodegenerative disease for which inhibition of autophagy would be suitable. Typically, the subject suffers from amyotrophic lateral sclerosis. As used herein, the term "amyotrophic lateral sclerosis (ALS)" includes the spectrum of neurodegenerative syndromes known under the names of Classical (Charcot's) ALS, Lou Gehrig's disease, motor neuron disease (MND), progressive bulbar palsy (PBP), progressive muscular atrophy (PMA), primary lateral sclerosis (PLS), bulbar onset ALS, spinal onset ALS and ALS with multi-system involvement (Wijesekera L C and Leigh P N. Amyotrophic lateral sclerosis. Orphanet).

In some embodiments, the subject suffers from sarcopenia. As used herein, the term "sarcopenia" means the gradual decrease in skeletal muscle mass caused by aging, which can directly cause a decrease in muscle strength, resulting in a decrease and impairment in various physical functions.

Agents that Promote the Activity or Expression of DBI:

In some embodiments, the agent that promotes the activity of DBI is a polypeptide having at least having at least 80% of identity with the sequence of SEQ ID NO:1 or a fragment thereof.

According to the invention a first amino acid sequence having at least 80% of identity with a second amino acid sequence means that the first sequence has 80, 81, 82, 83, 84, 85, 86, 87, 88, 89, 90; 91; 92; 93; 94; 95; 96; 97; 98; 99 or 100% of identity with the second amino acid sequence. Sequence identity is frequently measured in terms of percentage identity (or similarity or homology); the higher the percentage, the more similar are the two sequences. Methods of alignment of sequences for comparison are well known in the art. Various programs and alignment algorithms are described in: Smith and Waterman, Adv. Appl. Math., 2:482, 1981; Needleman and Wunsch, J. Mol. Biol., 48:443, 1970; Pearson and Lipman, Proc. Natl. Acad. Sci. U.S.A., 85:2444, 1988; Higgins and Sharp, Gene, 73:237-244, 1988; Higgins and Sharp, CABIOS, 5:151-153, 1989; Corpet et al. Nuc. Acids Res., 16:10881-10890, 1988; Huang et al., Comp. Appls Biosci., 8:155-165, 1992; and Pearson et al., Meth. Mol. Biol., 24:307-31, 1994). Altschul et al., Nat. Genet., 6:119-129, 1994, presents a detailed consideration of sequence alignment methods and homology calculations. By way of example, the alignment tools ALIGN (Myers and Miller, CABIOS 4:11-17, 1989) or LFASTA (Pearson and Lipman, 1988) may be used to perform sequence comparisons (Internet Program® 1996, W. R. Pearson and the University of Virginia, fasta20u63 version 2.0u63, release date December 1996). ALIGN compares entire sequences against one another, while LFASTA compares regions of local similarity. These alignment tools and their respective tutorials are available on the Internet at the NCSA Website, for instance. Alternatively, for comparisons of amino acid sequences of greater than about 30 amino acids, the Blast 2 sequences function can be employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). The BLAST sequence comparison system is available, for instance, from the NCBI web site; see also Altschul et al., J. Mol. Biol., 215:403-410, 1990; Gish. & States, Nature Genet., 3:266-272, 1993; Madden et al. Meth. Enzymol., 266:131-141, 1996; Altschul et al., Nucleic Acids Res., 25:3389-3402, 1997; and Zhang & Madden, Genome Res., 7:649-656, 1997.

As used herein, the term "fragment" refers to a physically contiguous portion of the primary structure of the polypeptide (i.e. SEQ ID NO:1). In some embodiments, the fragment comprises at least 8 consecutive amino acids of SEQ ID NO:1. In some embodiments, the fragment comprises 8; 9; 10; 11; 12; 13; 14; 15; 16; 17; 18; 19; 20; 21; 22; 23; 24; 25; 26; 27; 28; 29; 30; 31; 32; 33; 34; 35; 36; 37; 38; 39; 40; 41; 42; 43; 44; 45; 46; 47; 48; 49; 50; 51; 52; 53; 54; 55; 56; 57; 58; 59; 60; 61; 62; 63; 64; 65; 66; 67; 68; 69; 70; 71; 72; 73; 74; 75; 76; 77; 78; 79; 80; 81: 82; 83; 84; 85; or 86 consecutive amino acids. According to the present invention the fragment shall retain the activity of DBI.

In some embodiments, the fragment consist in the amino acid sequence ranging from the amino acid residue at position 17 to the amino acid residue at position 50 (i.e. the triacontatetraneuropeptide or TTN).

In some embodiments, the fragment consists in the amino acid sequence ranging from the amino acid residue at position 33 to the amino acid residue at position 50 (i.e. the octadecaneuropeptide or ODN).

In some embodiments, the fragment consists in the amino acid sequence ranging from the amino acid residue at position 43 to the amino acid residue at position 50 (i.e. the octapeptide or OP).

Accordingly, in some embodiments, the agent that promotes the activity of DBI consists in a polypeptide comprising:
   an amino acid sequence having at least 80% of identity with SEQ ID NO:1, or
   an amino acid sequence having at least 80% of identity with the amino acid sequence ranging from the amino acid residue at position 17 to the amino acid residue at position 50 in SEQ ID NO:1, or
   an amino acid sequence having at least 80% of identity with the amino acid sequence ranging from the amino acid residue at position 33 to the amino acid residue at position 50 in SEQ ID NO:1, or
   an amino acid sequence having at least 80% of identity with the amino acid sequence ranging from the amino acid residue at position 43 to the amino acid residue at position 50 in SEQ ID NO:1.

In some embodiments, the polypeptide of the present invention is fused to at least one heterologous polypeptide to form a fusion protein. In some embodiments, the polypeptide of the present invention is fused either directly or via a spacer at its C-terminal end to the N-terminal end of the heterologous polypeptide, or at its N-terminal end to the C-terminal end of the heterologous polypeptide. As used herein, the term "directly" means that the (first or last) amino acid at the terminal end (N or C-terminal end) of the polypeptide of the present invention is fused to the (first or last) amino acid at the terminal end (N or C-terminal end) of the heterologous polypeptide. In other words, in this embodiment, the last amino acid of the C-terminal end of said polypeptide is directly linked by a covalent bond to the first amino acid of the N-terminal end of said heterologous polypeptide, or the first amino acid of the N-terminal end of said polypeptide is directly linked by a covalent bond to the last amino acid of the C-terminal end of said heterologous polypeptide. As used herein, the term "spacer" refers to a sequence of at least one amino acid that links the polypeptide of the invention to the heterologous polypeptide. Such a spacer may be useful to prevent steric hindrances. Typically a spacer comprises 2, 3; 4; 5; 6; 7; 8; 9; 10; 11; 12; 13; 14; 15; 16; 17; 18; 19; or 20 amino acids.

In some embodiments, the polypeptide of the present invention is fused to a signal sequence. A signal sequence can be used to facilitate secretion and isolation of the secreted protein or other proteins of interest. Signal sequences are typically characterized by a core of hydrophobic amino acids which are generally cleaved from the mature protein during secretion in one or more cleavage events. Such signal peptides contain processing sites that allow cleavage of the signal sequence from the mature proteins as they pass through the secretory pathway.

In some embodiments, the fusion protein according to the invention is an immunoadhesin. As used herein, the term "immunoadhesin" designates antibody-like molecules which combine the binding specificity of the polypeptide of the present invention with the effector functions of immunoglobulin constant domains. Structurally, the immunoadhesins comprise a fusion of the polypeptide of the present invention and an immunoglobulin constant domain sequence. The immunoglobulin constant domain sequence in the immunoadhesin may be obtained from any immunoglobulin, such as IgG-1, IgG-2, IgG-3, or IgG-4 subtypes, IgA (including IgA-1 and IgA-2), IgE, IgD or IgM. The immunoglobulin sequence typically, but not necessarily, is an immunoglobulin constant domain (Fc region). Immunoadhesins can possess many of the valuable chemical and biological properties of human antibodies. Since immunoadhesins can be constructed from a human protein sequence with a desired specificity linked to an appropriate human immunoglobulin hinge and constant domain (Fc) sequence, the binding specificity of interest can be achieved using entirely human components. Such immunoadhesins are minimally immunogenic to the patient, and are safe for chronic or repeated use. In some embodiments, the Fc region is a native sequence Fc region. In some embodiments, the Fc region is a variant Fc region. In still another embodiment, the Fc region is a functional Fc region. As used herein, the term "Fc region" is used to define a C-terminal region of an immunoglobulin heavy chain, including native sequence Fc regions and variant Fc regions. Although the boundaries of the Fc region of an immunoglobulin heavy chain might vary, the human IgG heavy chain Fc region is usually defined to stretch from an amino acid residue at position Cys226, or from Pro230, to the carboxyl-terminus thereof. The adhesion portion and the immunoglobulin sequence portion of the immunoadhesin may be linked by a minimal linker. The immunoglobulin sequence typically, but not necessarily, is an immunoglobulin constant domain. The immunoglobulin moiety in the chimeras of the present invention may be obtained from IgG1, IgG2, IgG3 or IgG4 subtypes, IgA, IgE, IgD or IgM, but typically IgG1 or IgG3. In some embodiments, the polypeptide of the invention and the immunoglobulin sequence portion of the immunoadhesin are linked by a minimal linker. As used herein, the term "linker" refers to a sequence of at least one amino acid that links the polypeptide of the invention and the immunoglobulin sequence portion. Such a linker may be useful to prevent steric hindrances. In some embodiments, the linker has 4; 5;

6; 7; 8; 9; 10; 11; 12; 13; 14; 15; 16; 17; 18; 19; 20; 21; 22; 23; 24; 25; 26; 27; 28; 29; 30 amino acid residues. However, the upper limit is not critical but is chosen for reasons of convenience regarding e.g. biopharmaceutical production of such polypeptides. The linker sequence may be a naturally occurring sequence or a non-naturally occurring sequence. If used for therapeutical purposes, the linker is preferably non-immunogenic in the subject to which the immunoadhesin is administered. One useful group of linker sequences are linkers derived from the hinge region of heavy chain antibodies as described in WO 96/34103 and WO 94/04678. Other examples are poly-alanine linker sequences.

The polypeptides of the present invention are produced by any technique known per se in the art, such as, without limitation, any chemical, biological, genetic or enzymatic technique, either alone or in combination. For instance, knowing the amino acid sequence of the desired sequence, one skilled in the art can readily produce said polypeptides, by standard techniques for production of amino acid sequences. For instance, they can be synthesized using well-known solid phase method, preferably using a commercially available peptide synthesis apparatus (such as that made by Applied Biosystems, Foster City, California) and following the manufacturer's instructions. Alternatively, the polypeptides of the present invention can be synthesized by recombinant DNA techniques as is now well-known in the art. For example, these fragments can be obtained as DNA expression products after incorporation of DNA sequences encoding the desired (poly)peptide into expression vectors and introduction of such vectors into suitable eukaryotic or prokaryotic hosts that will express the desired polypeptide, from which they can be later isolated using well-known techniques.

In some embodiments, it is contemplated that the polypeptide of the invention used in the therapeutic methods of the present invention may be modified in order to improve their therapeutic efficacy. Such modification of therapeutic compounds may be used to decrease toxicity, increase circulatory time, or modify biodistribution. For example, the toxicity of potentially important therapeutic compounds can be decreased significantly by combination with a variety of drug carrier vehicles that modify biodistribution. A strategy for improving drug viability is the utilization of water-soluble polymers. Various water-soluble polymers have been shown to modify biodistribution, improve the mode of cellular uptake, change the permeability through physiological barriers; and modify the rate of clearance from the body. To achieve either a targeting or sustained-release effect, water-soluble polymers have been synthesized that contain drug moieties as terminal groups, as part of the backbone, or as pendent groups on the polymer chain. Polyethylene glycol (PEG) has been widely used as a drug carrier, given its high degree of biocompatibility and ease of modification. Attachment to various drugs, proteins, and liposomes has been shown to improve residence time and decrease toxicity. PEG can be coupled to active agents through the hydroxyl groups at the ends of the chain and via other chemical methods; however, PEG itself is limited to at most two active agents per molecule. In a different approach, copolymers of PEG and amino acids were explored as novel biomaterials which would retain the biocompatibility properties of PEG, but which would have the added advantage of numerous attachment points per molecule (providing greater drug loading), and which could be synthetically designed to suit a variety of applications.

In some embodiments, the agent that promotes the expression of DBI is a nucleic acid molecule that encodes for the polypeptide as described above. As used herein, the term "nucleic acid molecule" has its general meaning in the art and refers to a DNA or RNA molecule. However, the term captures sequences that include any of the known base analogues of DNA and RNA such as, but not limited to 4-acetylcytosine, 8-hydroxy-N6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethyl-aminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyamino-methyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, -uracil-5-oxyacetic acid methylester, uracil-5-oxyacetic acid, pseudouracil, queosine, 2-thiocytosine, and 2,6-diaminopurine.

In some embodiments, the nucleic acid molecule comprises a nucleic acid sequence having at least 50% with SEQ ID NO: 2. According to the invention a first nucleic acid sequence having at least 50% of identity with a second nucleic acid sequence means that the first sequence has 50; 51; 52; 53; 54; 55; 56; 57; 58; 59; 60; 61; 62; 63; 64; 65; 66; 67; 68; 69; 70; 71; 72; 73; 74; 75; 76; 77; 78; 79; 80; 81; 82; 83; 84; 85; 86; 87; 88; 89; 90; 91; 92; 93; 94; 95; 96; 97; 98; 99; or 100% of identity with the second nucleic acid sequence.

In some embodiments, the nucleic acid molecule of the present invention is included in a suitable vector, such as a plasmid, cosmid, episome, artificial chromosome, phage or a viral vector. Typically, the vector is a viral vector which is an adeno-associated virus (AAV), a retrovirus, bovine papilloma virus, an adenovirus vector, a lentiviral vector, a vaccinia virus, a polyoma virus, or an infective virus. In some embodiments, the vector is an AAV vector. As used herein, the term "AAV vector" means a vector derived from an adeno-associated virus serotype, including without limitation, AAV1, AAV2, AAV3, AAV4, AAV5, AAV6, AAV7, AAV8, AAV9, and mutated forms thereof. AAV vectors can have one or more of the AAV wild-type genes deleted in whole or part, preferably the rep and/or cap genes, but retain functional flanking ITR sequences. Retroviruses may be chosen as gene delivery vectors due to their ability to integrate their genes into the host genome, transferring a large amount of foreign genetic material, infecting a broad spectrum of species and cell types and for being packaged in special cell-lines. In order to construct a retroviral vector, a nucleic acid encoding a gene of interest is inserted into the viral genome in the place of certain viral sequences to produce a virus that is replication-defective. In order to produce virions, a packaging cell line is constructed containing the gag, pol, and/or env genes but without the LTR and/or packaging components. When a recombinant plasmid containing a cDNA, together with the retroviral LTR and packaging sequences is introduced into this cell line (by calcium phosphate precipitation for example), the packaging sequence allows the RNA transcript of the recombinant plasmid to be packaged into viral particles, which are then secreted into the culture media. The media containing the recombinant retroviruses is then collected, optionally concentrated, and used for gene transfer. Retroviral vectors are able to infect a broad variety of cell types. Lentiviruses are complex retroviruses, which, in addition to the common retroviral genes gag, pol, and env, contain other genes with regulatory or structural function. The higher complexity enables the virus to modulate its life cycle, as in the course of latent infection. Some examples of lentivirus include the Human Immunodeficiency Viruses (HIV 1, HIV 2) and the Simian Immunodeficiency Virus (SIV). Lentiviral vectors have been generated by multiply attenuating the HIV virulence genes, for example, the genes env, vif, vpr, vpu and nef are deleted making the vector biologically safe. Lentiviral vectors are known in the art, see, e.g. U.S. Pat. Nos. 6,013,516 and 5,994,136, both of which are incorporated herein by reference. In general, the vectors are plasmid-based or virus-based, and are configured to carry the essential sequences for incorporating foreign nucleic acid, for selection and for transfer of the nucleic acid into a host cell. The gag, pol and env genes of the vectors of interest also are known in the art. Thus, the relevant genes are cloned into the selected vector and then used to transform the target cell of interest. Recombinant lentivirus capable of infecting a non-dividing cell wherein a suitable host cell is transfected with two or more vectors carrying the packaging functions, namely gag, pol and env, as well as rev and tat is described in U.S. Pat. No. 5,994,136, incorporated herein by reference. This describes a first vector that can provide a nucleic acid encoding a viral gag and a pol gene and another vector that can provide a nucleic acid encoding a viral env to produce a packaging cell. Introducing a vector providing a heterologous gene into that packaging cell yields a producer cell which releases infectious viral particles carrying the foreign gene of interest. The env preferably is an amphotropic envelope protein which allows transduction of cells of human and other species. Typically, the nucleic acid molecule or the vector of the present invention include "control sequences", which refers collectively to promoter sequences, polyadenylation signals, transcription termination sequences, upstream regulatory domains, origins of replication, internal ribosome entry sites ("IRES"), enhancers, and the like, which collectively provide for the replication, transcription and translation of a coding sequence in a recipient cell. Not all of these control sequences need always be present so long as the selected coding sequence is capable of being replicated, transcribed and translated in an appropriate host cell. Another nucleic acid sequence, is a "promoter" sequence, which is used herein in its ordinary sense to refer to a nucleotide region comprising a DNA regulatory sequence, wherein the regulatory sequence is derived from a gene which is capable of binding RNA polymerase and initiating transcription of a downstream (3'-direction) coding sequence. Transcription promoters can include "inducible promoters" (where expression of a polynucleotide sequence operably linked to the promoter is induced by an analyte, cofactor, regulatory protein, etc.), "repressible promoters" (where expression of a polynucleotide sequence operably linked to the promoter is induced by an analyte, cofactor, regulatory protein, etc.), and "constitutive promoters".

In some embodiments, the agent that promotes the activity of DBI is a small organic molecule or peptidomimetics that mimics the activity of DBI. As used herein, the term "small organic molecule" refers to a molecule of a size comparable to those organic molecules generally used in pharmaceuticals. The term excludes biological macromolecules (e. g., proteins, nucleic acids, etc.). Preferred small organic molecules range in size up to about 5000 Da, more preferably up to 2000 Da, and most preferably up to about 1000 Da. As used herein, the term "peptidomimetics" is used to refer to any molecule whose essential elements (pharmacophore) mimic a natural peptide or protein in 3D space and which retain the ability to interact with the biological target and produce the same biological effect. Peptidomimetics include small protein-like chain designed to mimic a peptide which may typically be obtained either by modifying an existing peptide, or by designing similar systems that mimic peptides, such as, e.g., peptoids and β-peptides. Irrespective of the approach, the altered chemical structure is designed to adjust the molecular properties advantageously in that, e.g., the stability or biological activity is increased or decreased. According modifications involve changes to the peptide that will not occur naturally including but not limited to altered backbones and the incorporation of non-natural amino acids. The term "amino acid mimetics," as used herein, refers to chemical compounds that have a structure that is different from the general chemical structure of an amino acid, but functions in a manner similar to a naturally occurring amino acid.

Methods of Stimulating Autophagy:

Accordingly, the first object of the present invention relates to a method of stimulating autophagy in a subject in need thereof comprising administering to the subject a therapeutically effective amount of an agent that inhibits the activity or expression of DBI.

In some embodiments, the method of stimulating autophagy according to the invention is particularly suitable for inhibiting appetite and consequently weight loss. The method is also particularly for reducing glycaemia and lipogenesis. Accordingly, the method of the present invention is particularly suitable for the treatment of various diseases as described herein after.

In some embodiments, the subject is overweight. In particular, the subject is obese. Obesity refers to a condition whereby an otherwise healthy subject has a BMI greater than or equal to 30 kg/m$^2$, or a condition whereby a subject with at least one co-morbidity has a BMI greater than or equal to 27 kg/m$^2$. An "obese subject" is an otherwise healthy subject with a BMI greater than or equal to 30 kg/m$^2$ or a subject with at least one co-morbidity with a BMI greater than or equal 27 kg/m$^2$. A "subject at risk of obesity" is an otherwise healthy subject with a BMI of 25 kg/m$^2$ to less than 30 kg/m$^2$ or a subject with at least one co-morbidity with a BMI of 25 kg/m$^2$ to less than 27 kg/m$^2$. The increased risks associated with obesity may occur at a lower BMI in people of Asian descent. In Asian and Asian-Pacific countries, including Japan, "obesity" refers to a condition whereby a subject has a BMI greater than or equal to 25 kg/m$^2$. An "obese subject" in these countries refers to a subject with at least one obesity-induced or obesity-related co-morbidity that requires weight reduction or that would be improved by weight reduction, with a BMI greater than or equal to 25 kg/m$^2$. In these countries, a "subject at risk of obesity" is a person with a BMI of greater than 23 kg/m2 to less than 25 kg/m$^2$.

In some embodiments, the subject suffers from type 2 diabetes. As used herein, the term "type 2 diabetes" or "non-insulin dependent diabetes mellitus (NIDDM)" has its general meaning in the art. Type 2 diabetes often occurs when levels of insulin are normal or even elevated and appears to result from the inability of tissues to respond appropriately to insulin. Most of the Type 2 diabetics are obese.

In some embodiments, the subject suffers from metabolic syndrome. As used herein, the term "Metabolic Syndrome" refers to a subject characterized by having three or more of the following symptoms: abdominal obesity, hyperglyceridemia, low HDL cholesterol, high blood pressure, and high fasting plasma glucose. The criteria for these symptoms are defined in the third Report of the National Cholesterol Education Program Expert Panel in Detection, Evaluation and Treatment of High blood Cholesterol in Adults (Ford, E S. et al. 2002).

In some embodiments, the subject suffers from a cancer. Although the underlying mechanism has not been characterized yet, it has been shown that pre-chemotherapy starvation (the most potent autophagy-inducing physiological stimulus able to systemically induce autophagy) significantly increased treatment efficiency and limits the tumour growth. Furthermore, it has been demonstrated that tumours with PI3K over-activation are resistant to dietary restriction, suggesting an important role for autophagy in the chemio-sensitization process. This invention might lead to a less aggressive and equivalently effective treatment based on the punctual administration of an agent of the present invention. Accordingly, a further object of the present invention relates to a method for treating a cancer in a subject in need thereof comprising administering the subject with a therapeutically effective amount of agent of the present invention and a therapeutically effective amount of a chemotherapeutic agent wherein the agent of the present invention is administered prior to the chemotherapeutic agent. In some embodiments, the agent of the present invention is administered 12; 13; 14; 15; 16; 17; 18; 19; 20; 21; 22; 23; 24; 25; 26; 27; 28; 29; 30; 31; 32; 33; 34; 35; 36; 37; 38; 39; 40; 41; 42; 43; 44; 45; 46; 47; 48; 49; 50; 51; 52; 53; 54; 55; 56 h before the administration of the chemotherapeutic agent. Chemotherapeutic agents include, but are not limited to alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammaII and calicheamicin omegaII; dynemicin, including dynemicin A; bisphosphonates, such as clodronate; an esperamicin; as well as neocarzinostatin chromophore and related chromoprotein enediyne antiobiotic chromophores, aclacinomysins, actinomycin, authrarnycin, azaserine, bleomycins, cactinomycin, carabicin, caminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxy doxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK polysaccharide complex); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., paclitaxel and doxetaxel; chlorambucil; gemcitabine; 6-thioguanine; mercaptopurine; methotrexate; platinum coordination complexes such as cisplatin, oxaliplatin and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-1 1); topoisomerase inhibitor RFS 2000; difluoromethylomithine (DMFO); retinoids such as retinoic acid; capecitabine; and pharmaceutically acceptable salts, acids or derivatives of any of the above.

In some embodiments, the subject suffers from a neurodegenerative disease. Examples of neurodegenerative diseases include but are not limited to Adrenoleukodystrophy (ALD), Alexander's disease, Alper's disease, Alzheimer's disease, Amyotrophic lateral sclerosis (Lou Gehrig's Disease), Ataxia telangiectasia, Batten disease (also known as Spielmeyer-Vogt-Sjögren-Batten disease), Bovine spongiform encephalopathy (BSE), Canavan disease, Cockayne syndrome, Corticobasal degeneration, Creutzfeldt-Jakob disease, Frontotemporal lobar degeneration, Huntington's disease, HIV-associated dementia, Kennedy's disease, Krabbe's disease, Lewy body dementia, Neuroborreliosis, Machado-Joseph disease (Spinocerebellar ataxia type 3), MELAS—Mitochondrial Encephalopathy, Lactic Acidosis and Stroke, Multiple System Atrophy, Multiple sclerosis, Niemann Pick disease, Parkinson's disease, Pelizaeus-Merzbacher Disease, Pick's disease, Primary lateral sclerosis, Prion diseases, Progressive Supranuclear Palsy, Refsum's disease, Sandhoff disease, Schilder's disease, Spinocerebellar ataxia (multiple types with varying characteristics), Spinal muscular atrophy, Steele-Richardson-Olszewski disease, Tabes dorsalis, Tay-Sachs Disease, and Toxic encephalopathy. Preferred neurodegenerative diseases include Alzheimer's disease. Neurodegenerative diseases (i.e Alzheimer disease, Parkinson disease, Huntington disease) are a series of different age-dependent or genetic-dependent pathologies, characterized by progressive neuronal death as consequence of accumulation of aggregates of misfolded proteins, damaged organelles, impaired function of cellular clearence mechanisms. Being autophagy a physiological mechanism dedicated to the degradation of potentially harmful and aggregation-prone long-lived proteins, as well as of the recycle of damaged organelles, it is considered as a protective factor against neuronal cell death. In the context of this invention, the treatment of patients with agent of the present invention may results in an improvement of the cellular clearance functions and in an amelioration of the symptomatology of different diseases. For example, Huntington disease is a pathology characterized by the progressive expansion of poly-glutamine tail of the protein huntingtin, resulting in its intra-neuronal aggregation. Huntingtin has been demonstrated to be a specific target of the autophagic pathway, and the increase in basal autophagy by administration of the agent of the present invention can reduce the rate of neuronal death. In two forms of familiar Parkinson disease, recessive mutations in two genes encoding for PINK1 and PARK2, involved in mitophagy, partially account for the pathogenesis of this disease and may render the patients suitable for treatment with agent of the present invention. In the same way, autophagy induction may contribute to the removal of alpha-synuclein aggregates (Lewi bodies), responsible for the pathogenesis of sporadic forms of Parkinson disease, most likely due to a saturation of the autophagic system.

In some embodiments, the subject suffers from an infectious disease. Autophagic process actively participates in a multipronged defense against microorganisms, contributing to their elimination either via the selective delivery of microorganisms to degradative lysosomes (a process referred to as xenophagy) or via the delivery of microbial nucleic acids to endolysosomal compartment (with subsequent activation of innate and adaptive immunity). Clinically relevant pathogens are degraded in vitro by xenophagy; among these, there are bacteria such as group A *Streptococcus pyogenes, Mycobacterium tuberculosis, Shigella flexneri, Salmonella enterica, Listeria monocytogenes*; viruses such as herpes simplex virus type 1 (HSV 1) and parasites such as *Toxoplasma gondii*. Moreover in vivo evidences showed that autophagy genes have a protective role against numerous pathogens, including *L. monocytogenes, M. tuberculosis, S. enterica, T. gondii*, HSV 1. It has been recently shown that the infection mediated by pathogens like *Shigella* and *Salmonella* triggers an aminoacids starvation response eventually leading to the elimination of these pathogens via autophagy. Here use of agent of the present invention for triggering a pro-autophagic and anti microbial response against bacterial and virus infection may be suitable.

In some embodiments, the subject suffers from pulmonary emphysema. Mutations in the protein α1-antitrypsin causes pulmonary emphysema, a disease characterized by the accumulation of the aggregated form of the mutant proteins. As for others proteinopathy, autophagy induction by the administration of agent of the present invention (e.g. HC, UK-5099) might ameliorate the symptoms.

In some embodiments, the subject suffers from cystic fibrosis. A recent pre-clinical study has found as a consequence of a dysfunctional aggrephagy the pathogenicity of cystic fibrosis, due to an impaired clearance of aggregates of the mutant CTFR. Induction of autophagy mediated by administration of an agent of the present invention may represent a suitable strategy.

In some embodiments, the subject suffers from a liver disease. The potential impact of autophagy in vivo was discovered from liver studies and this underlines the important role played by autophagy in the physiology of liver.

Accordingly, a further object of the present invention relates to a method of treating a non-alcoholic fatty liver disease in a subject in thereof comprising administering to the subject a therapeutically effective amount of an agent that inhibits the activity or expression of DBI.

As used herein, the term "non-alcoholic fatty liver disease" or "NAFLD" has its general meaning in the art and refers to one cause of a fatty liver, occurring when fat is deposited in the liver not due to excessive alcohol use. Non-alcoholic fatty liver disease (NAFLD) represents one of the most recurrent and severe pathologies, especially among obese and diabetic patients, yet a specific therapy is far from being available. NAFLD is defined as the accumulation of fat in the liver, but not as secondary consequence of alcohol consumption. The pro-autophagic potential of agent of the present invention can be used as therapy for NAFLD for different causes: selective degradation of TG droplets (lipophagy), suppression of lipogenetic pathways (i.e. inhibition of Citrate export from the mitochondria by BTC). Conversely, autophagy inducer Perhexiline can play an adaptive and protective role in ALD, conferring to hepatocyte protection after ethanol intoxication and inhibiting adipocytes differentiation.

NAFLD can be sub-classified as non-alcoholic steatohepatitis (NASH) and nonalcoholic fatty liver (NAFL). Nonalcoholic fatty liver (NAFL) is a type of NAFLD and is a condition in which fat accumulates in the liver cells. NAFL has minimal risk of progressing to cirrhosis. Nonalcoholic steatohepatitis (NASH) is the more extreme form of NAFLD, and is regarded as a major cause of fibrosis and cirrhosis of the liver of unknown cause. The major feature in NASH is fat in the liver, along with inflammation and damage. NASH can be severe and can lead to fibrosis and cirrhosis, in which the liver is permanently damaged and scarred and no longer able to work properly. Most patients with NAFLD have few or no symptoms. Patients may complain of fatigue, malaise, and dull right-upper-quadrant abdominal discomfort. Mild jaundice may be noticed although this is rare. Accordingly the complications of NAFLD typically include liver fibrosis and subsequently cirrhosis. Liver fibrosis is characterized by the accumulation of extracellular matrix that can be distinguished qualitatively from that in normal liver. Left unchecked, hepatic fibrosis progresses to cirrhosis (defined by the presence of encapsulated nodules), liver and organ failure, and death.

In some embodiments, the agent that inhibits the activity or expression of DBI is particularly suitable for the treatment of NASH.

In some embodiments, the subject suffers from pancreatitis, which is an inflammatory disease of the exocrine pancreas, culminating in a massive necrotic cell death of acinar cells. Although the mechanisms promoting this pathology are still unclear, there is a consensus on the notion that autophagy is impaired in this pathological process. Acinar cells are characterized by large autophagosomes unable to become autophagolysosomes, mainly due to the depletion of lysosomal proteins (i.e. LAMP2). Furthermore, it has been recently shown that loss of Ikkα inhibits autophagy flux and promotes the formation of p62-positive protein aggregates, thus contributing to the initiation of the disease. In addition, during the acute phase of the disease, a selective autophagy process called 'zymophagy' prevents acinar cells death through degradation of harmful activated zymogen granules. agent of the present invention such as the hydroxycitric acid can be tested for their capacity to trigger zimophagy. Moreover, these agents, alone or in combination with a lysosomal-targeted therapy, can be suitable for ameliorating the symptomatology of the disease by restoring a normal autophagic flux.

In some embodiments, the subject suffers from a proteinopathy. Inducing autophagy by using agent of the present invention may be particularly suitable for the treatment of proteionpathies. Examples of proteinopathies include, but are not limited to Alzheimer's disease, cerebral β-amyloid angiopathy, retinal ganglion cell degeneration, prion diseases (e.g. bovine spongiform encephalopathy, kuru, Creutzfeldt-Jakob disease, variant Creutzfeldt-Jakob disease, Gerstmann-Straussler-Scheinker syndrome, fatal familial insomnia) tauopathies (e.g. frontotemporal dementia, Alzheimer's disease, progressive supranuclear palsy, corticobasal degeration, frontotemporal lobar degeneration), frontemporal lobar degeneration, amyotrophic lateral sclerosis, Huntington's disease, familial British dementia, Familial Danish dementia, hereditary cerebral hemorrhage with amyloidosis (Iclandic), CADASIL, Alexander disease, Seipinopathies, familial amyloidotic neuropathy, senile systemic amyloidosis, serpinopathies, AL amyloidosis, AA amyloidosis, type II diabetes, aortic medial amyloidosis, ApoAI amyloidosis, ApoII amyloidosis, ApoAIV amyloidosis, familial amyloidosis of the Finish type, lysozyme amyloidosis, fibrinogen amyloidosis, dialysis amyloidosis, inclusion body myositis/myopathy, cataracts, medullary thyroid carcinoma, cardiac atrial amyloidosis, pituitary prolactinoma, hereditary lattice corneal dystrophy, cutaneous lichen amyloidosis, corneal lactoferrin amyloidosis, corneal lactoferrin amyloidosis, pulmonary alveolar proteinosis, odontogenic tumor amylois, seminal vesical amyloid, cystic fibrosis, sickle cell disease and critical illness myopathy.

Agents that Inhibit the Activity or Expression of DBI:

In some embodiments, the agent that inhibits the activity of DBI is an antibody directed against DBI.

As used herein, the term "antibody" is thus used to refer to any antibody-like molecule that has an antigen binding region, and this term includes antibody fragments that comprise an antigen binding domain such as Fab', Fab, F(ab')2, single domain antibodies (DABs), TandAbs dimer, Fv, scFv (single chain Fv), dsFv, ds-scFv, Fd, linear antibodies, minibodies, diabodies, bispecific antibody fragments, bibody, tribody (scFv-Fab fusions, bispecific or trispecific, respectively); sc-diabody; kappa(lamda) bodies (scFv-CL fusions); BiTE (Bispecific T-cell Engager, scFv-scFv tandems to attract T cells); DVD-Ig (dual variable domain antibody, bispecific format); SIP (small immunoprotein, a kind of minibody); SMIP ("small modular immunopharmaceutical" scFv-Fc dimer; DART (ds-stabilized diabody "Dual Affinity ReTargeting"); small antibody mimetics comprising one or more CDRs and the like. The techniques for preparing and using various antibody-based constructs and fragments are well known in the art (see Kabat et al., 1991, specifically incorporated herein by reference). Diabodies, in particular, are further described in EP 404, 097 and WO 93/1 1 161; whereas linear antibodies are further described in Zapata et al. (1995). Antibodies can be fragmented using conventional techniques. For example, F(ab')2 fragments can be generated by treating the antibody with pepsin. The resulting F(ab')2 fragment can be treated to reduce disulfide bridges to produce Fab' fragments. Papain digestion can lead to the formation of Fab fragments. Fab, Fab' and F(ab')2, scFv, Fv, dsFv, Fd, dAbs, TandAbs, ds-scFv, dimers, minibodies, diabodies, bispecific antibody fragments and other fragments can also be synthesized by recombinant techniques or can be chemically synthesized. Techniques for producing antibody fragments are well known and described in the art. For example, each of Beckman et al., 2006; Holliger & Hudson, 2005; Le Gall et al., 2004; Reff & Heard, 2001; Reiter et al., 1996; and Young et al., 1995 further describe and enable the production of effective antibody fragments. In some embodiments, the antibody of the present invention is a single chain antibody. As used herein the term "single domain antibody" has its general meaning in the art and refers to the single heavy chain variable domain of antibodies of the type that can be found in Camelid mammals which are naturally devoid of light chains. Such single domain antibody is also called "nanobody®". For a general description of (single) domain antibodies, reference is also made to the prior art cited above, as well as to EP 0 368 684, Ward et al. (Nature 1989 Oct. 12; 341 (6242): 544-6), Holt et al., Trends Biotechnol., 2003, 21(11):484-490; and WO 06/030220, WO 06/003388.

In natural antibodies, two heavy chains are linked to each other by disulfide bonds and each heavy chain is linked to a light chain by a disulfide bond. There are two types of light chain, lambda (l) and kappa (k). There are five main heavy chain classes (or isotypes) which determine the functional activity of an antibody molecule: IgM, IgD, IgG, IgA and IgE. Each chain contains distinct sequence domains. The light chain includes two domains, a variable domain (VL) and a constant domain (CL). The heavy chain includes four domains, a variable domain (VH) and three constant domains (CHI, CH2 and CH3, collectively referred to as CH). The variable regions of both light (VL) and heavy (VH) chains determine binding recognition and specificity to the antigen. The constant region domains of the light (CL) and heavy (CH) chains confer important biological properties such as antibody chain association, secretion, transplacental mobility, complement binding, and binding to Fc receptors (FcR). The Fv fragment is the N-terminal part of the Fab fragment of an immunoglobulin and consists of the variable portions of one light chain and one heavy chain. The specificity of the antibody resides in the structural complementarity between the antibody combining site and the antigenic determinant. Antibody combining sites are made up of residues that are primarily from the hypervariable or complementarity determining regions (CDRs). Occasionally, residues from nonhypervariable or framework regions (FR) can participate to the antibody binding site or influence the overall domain structure and hence the combining site. Complementarity Determining Regions or CDRs refer to amino acid sequences which together define the binding affinity and specificity of the natural Fv region of a native immunoglobulin binding site. The light and heavy chains of an immunoglobulin each have three CDRs, designated L-CDR1, L-CDR2, L-CDR3 and H-CDR1, H-CDR2, H-CDR3, respectively. An antigen-binding site, therefore, typically includes six CDRs, comprising the CDR set from each of a heavy and a light chain V region. Framework Regions (FRs) refer to amino acid sequences interposed between CDRs. The residues in antibody variable domains are conventionally numbered according to a system devised by Kabat et al. This system is set forth in Kabat et al., 1987, in Sequences of Proteins of Immunological Interest, US Department of Health and Human Services, NIH, USA (hereafter "Kabat et al."). This numbering system is used in the present specification. The Kabat residue designations do not always correspond directly with the linear numbering of the amino acid residues in SEQ ID sequences. The actual linear amino acid sequence may contain fewer or additional amino acids than in the strict Kabat numbering corresponding to a shortening of, or insertion into, a structural component, whether framework or complementarity determining region (CDR), of the basic variable domain structure. The correct Kabat numbering of residues may be determined for a given antibody by alignment of residues of homology in the sequence of the antibody with a "standard" Kabat numbered sequence. The CDRs of the heavy chain variable domain are located at residues 31-35B (H-CDR1), residues 50-65 (H-CDR2) and residues 95-102 (H-CDR3) according to the Kabat numbering system. The CDRs of the light chain variable domain are located at residues 24-34 (L-CDR1), residues 50-56 (L-CDR2) and residues 89-97 (L-CDR3) according to the Kabat numbering system.

In some embodiments, the antibody is directed against the fragment consisting in the amino acid sequence ranging from the amino acid residue at position 43 to the amino acid residue at position 50 (i.e. the octapeptide or OP).

In some embodiments, the antibody of the present invention is a chimeric antibody, typically a chimeric mouse/human antibody. The term "chimeric antibody" refers to a monoclonal antibody which comprises a VH domain and a VL domain of an antibody derived from a non-human animal, a CH domain and a CL domain of a human antibody. As the non-human animal, any animal such as mouse, rat, hamster, rabbit or the like can be used. In particular, said mouse/human chimeric antibody may comprise the heavy chain and the light chain of the antibody of the present invention.

In some embodiments, the antibody is a humanized antibody. As used herein, "humanized" describes antibodies wherein some, most or all of the amino acids outside the CDR regions are replaced with corresponding amino acids derived from human immunoglobulin molecules. Methods of humanization include, but are not limited to, those described in U.S. Pat. Nos. 4,816,567, 5,225,539, 5,585,089, 5,693,761, 5,693,762 and 5,859,205, which are hereby incorporated by reference.

In some embodiments, the antibody is a fully human antibody. Fully human monoclonal antibodies also can be prepared by immunizing mice transgenic for large portions of human immunoglobulin heavy and light chain loci. See, e.g., U.S. Pat. Nos. 5,591,669, 5,598,369, 5,545,806, 5,545,807, 6,150,584, and references cited therein, the contents of which are incorporated herein by reference.

In some embodiments, the antibody is a neutralizing antibody. As used herein, the term "neutralizing antibody" is an antibody that that inhibits, reduces or completely the activity of DBI. Whether an antibody is a neutralizing antibody can be determined by in vitro assays described in the EXAMPLE. Typically, the neutralizing antibody of the present invention inhibits the activity of DBI by at least 50%, 60%, 70%, 80%, 90%, 95%, 99%, or 100%.

In some embodiments, the neutralizing antibody of the present invention does not mediate antibody-dependent cell-mediated cytotoxicity and thus does not comprise an Fc portion that induces antibody dependent cellular cytotoxicity (ADCC). In some embodiments, the neutralizing antibody does not comprise an Fc domain capable of substantially binding to a FcgRIIIA (CD16) polypeptide. In some embodiments, the neutralizing antibody lacks an Fc domain (e.g. lacks a CH2 and/or CH3 domain) or comprises an Fc domain of IgG2 or IgG4 isotype. In some embodiments, the neutralizing antibody consists of or comprises a Fab, Fab', Fab'-SH, F (ab') 2, Fv, a diabody, single-chain antibody fragment, or a multispecific antibody comprising multiple different antibody fragments. In some embodiments, the neutralizing antibody is not linked to a toxic moiety. In some embodiments, one or more amino acids selected from amino acid residues can be replaced with a different amino acid residue such that the antibody has altered C2q binding and/or reduced or abolished complement dependent cytotoxicity (CDC). This approach is described in further detail in U.S. Pat. No. 6,194,551 by ldusogie et al.

In some embodiments, the agents that inhibits the activity of DBI is an aptamer directed against DBI. Aptamers are a class of molecule that represents an alternative to antibodies in term of molecular recognition. Aptamers are oligonucleotide sequences with the capacity to recognize virtually any class of target molecules with high affinity and specificity. Such ligands may be isolated through Systematic Evolution of Ligands by EXponential enrichment (SELEX) of a random sequence library. The random sequence library is obtainable by combinatorial chemical synthesis of DNA. In this library, each member is a linear oligomer, eventually chemically modified, of a unique sequence. Peptide aptamers consists of a conformationally constrained antibody variable region displayed by a platform protein, such as *E. coli* Thioredoxin A that are selected from combinatorial libraries by two hybrid methods (Colas et al., 1996).

In some embodiments, the agent that inhibits the expression of DBI is an inhibitor of expression. An "inhibitor of expression" refers to a natural or synthetic compound that has a biological effect to inhibit the expression of a gene. In a preferred embodiment of the invention, said inhibitor of gene expression is a siRNA, an endonuclease, an antisense oligonucleotide or a ribozyme.

In some embodiments, the inhibitor of expression is a siRNA. Small inhibitory RNAs (siRNAs) can also function as inhibitors of expression for use in the present invention. DBI gene expression can be reduced by contacting a patient or cell with a small double stranded RNA (dsRNA), or a vector or construct causing the production of a small double stranded RNA, such that DBI gene expression is specifically inhibited (i.e. RNA interference or RNAi).

In some embodiments, the inhibitor of expression is an endonuclease. The term "endonuclease" refers to enzymes that cleave the phosphodiester bond within a polynucleotide chain. Some, such as Deoxyribonuclease I, cut DNA relatively nonspecifically (without regard to sequence), while many, typically called restriction endonucleases or restriction enzymes, cleave only at very specific nucleotide sequences. The mechanism behind endonuclease-based genome inactivating generally requires a first step of DNA single or double strand break, which can then trigger two distinct cellular mechanisms for DNA repair, which can be exploited for DNA inactivating: the error prone non-homologous end-joining (NHEJ) and the high-fidelity homology-directed repair (HDR). In a particular embodiment, the endonuclease is CRISPR-Cas. As used herein, the term "CRISPR-Cas" has its general meaning in the art and refers to clustered regularly interspaced short palindromic repeats associated which are the segments of prokaryotic DNA containing short repetitions of base sequences. In some embodiment, the endonuclease is CRISPR-cas9, which is from *Streptococcus pyogenes*. The CRISPR/Cas9 system has been described in U.S. Pat. No. 8,697,359 B1 and US 2014/0068797. In some embodiment, the endonuclease is CRISPR-Cpf1 which is the more recently characterized CRISPR from Provotella and Francisella 1 (Cpf1) in Zetsche et al. ("Cpf1 is a Single RNA-guided Endonuclease of a Class 2 CRISPR-Cas System (2015); Cell; 163, 1-13).

In some embodiments, the inhibitor of expression is an antisense oligonucleotide. The term "antisense oligonucleotide" refers to an oligonucleotide sequence that is inverted relative to its normal orientation for transcription and so expresses an RNA transcript that is complementary to a target gene mRNA molecule expressed within the host cell (e.g., it can hybridize to the target gene mRNA molecule through Watson-Crick base pairing). An antisense strand may be constructed in a number of different ways, provided that it is capable of interfering with the expression of a target gene. For example, the antisense strand can be constructed by inverting the coding region (or a portion thereof) of the target gene relative to its normal orientation for transcription to allow the transcription of its complement, (e.g., RNAs encoded by the antisense and sense gene may be complementary). Furthermore, the antisense oligonucleotide strand need not have the same intron or exon pattern as the target gene, and noncoding segments of the target gene may be equally effective in achieving antisense suppression of target gene expression as coding segments. As used herein, the term "oligonucleotide" refers to a nucleic acid sequence, 3-5' or 5'-3' oriented, which may be single- or double-stranded. The antisense oligonucleotide used in the context of the invention may in particular be DNA or RNA. According to the invention, the antisense oligonucleotide of the present invention targets an mRNA encoding DBI (e.g. SEQ ID NO:2), and is capable of reducing the amount of DBI in cells. As used herein, an oligonucleotide that "targets" an mRNA refers to an oligonucleotide that is capable of specifically binding to said mRNA. That is to say, the antisense oligonucleotide comprises a sequence that is at least partially complementary, preferably perfectly complementary, to a region of the sequence of said mRNA, said complementarity being sufficient to yield specific binding under intra-cellular conditions. As immediately apparent to the skilled in the art, by a sequence that is "perfectly complementary to" a second sequence is meant the reverse complement counterpart of the second sequence, either under the form of a DNA molecule or under the form of a RNA molecule. A sequence is "partially complementary to" a second sequence if there are one or more mismatches. The antisense oligonucleotide of the present invention that target an mRNA encoding DBI may be designed by using the sequence of said mRNA as a basis, e.g. using bioinformatic tools. For example, the sequence of SEQ ID NO: 2 can be used as a basis for designing nucleic acids that target an mRNA encoding DBI. Preferably, the antisense oligonucleotide according to the invention is capable of reducing the amount of DBI in cells, e.g. in cancerous cells. Methods for determining whether an oligonucleotide is capable of reducing the amount of DBI in cells are known to the skilled in the art. This may for example be done by analyzing DBI protein expression by Western blot, and by comparing DBI protein expression in the presence and in the absence of the antisense oligonucleotide to be tested. In some embodiments, the antisense oligonucleotide of the present invention has a length of from 12 to 50 nucleotides, e.g. 12 to 35 nucleotides, from 12 to 30, from 12 to 25, from 12 to 22, from 15 to 35, from 15 to 30, from 15 to 25, from 15 to 22, from 18 to 22, or about 19, 20 or 21 nucleotides. The antisense oligonucleotide according to the invention may for example comprise or consist of 12 to 50 consecutive nucleotides, e.g. 12 to 35, from 12 to 30, from 12 to 25, from 12 to 22, from 15 to 35, from 15 to 30, from 15 to 25, from 15 to 22, from 18 to 22, or about 19, 20 or 21 consecutive nucleotides of a sequence complementary to the mRNA of SEQ ID NO: 2. In some embodiments, the antisense oligonucleotide of the present invention is further modified, preferably chemically modified, in order to increase the stability and/or therapeutic efficiency of the antisense oligonucleotide in vivo. In particular, the antisense oligonucleotide used in the context of the invention may comprise modified nucleotides. Chemical modifications may occur at three different sites: (i) at phosphate groups, (ii) on the sugar moiety, and/or (iii) on the entire backbone structure of the antisense oligonucleotide. For example, the antisense oligonucleotide may be employed as phosphorothioate derivatives (replacement of a non-bridging phosphoryl oxygen atom with a sulfur atom) which have increased resistance to nuclease digestion. 2'-methoxyethyl (MOE) modification (such as the modified backbone commercialized by ISIS Pharmaceuticals) is also effective. Additionally or alternatively, the antisense oligonucleotide of the present invention may comprise completely, partially or in combination, modified nucleotides which are derivatives with substitutions at the 2' position of the sugar, in particular with the following chemical modifications: O-methyl group (2'-O—Me) substitution, 2-methoxyethyl group (2'-O—MOE) substitution, fluoro group (2'-fluoro) substitution, chloro group (2'-Cl) substitution, bromo group (2'-Br) substitution, cyanide group (2'-CN) substitution, trifluoromethyl group (2'-CF3) substitution, OCF3 group (2'-OCF3) substitution, OCN group (2'-OCN) substitution, O-alkyl group (2'-O-alkyl) substitution, S-alkyl group (2'-S-alkyl) substitution, N-alkyl group (2'-N-akyl) substitution, O-alkenyl group (2'-O-alkenyl) substitution, S-alkenyl group (2'-S-alkenyl) substitution, N-alkenyl group (2'-N-alkenyl) substitution, SOCH3 group (2'-SOCH3) substitution, SO2CH3 group (2'-SO2CH3) substitution, ONO2 group (2'-ONO2) substitution, NO2 group (2'-NO2) substitution, N3 group (2'-N3) substitution and/or NH2 group (2'-NH2) substitution. Additionally or alternatively, the antisense oligonucleotide of the present invention may comprise completely or partially modified nucleotides wherein the ribose moiety is used to produce locked nucleic acid (LNA), in which a covalent bridge is formed between the 2' oxygen and the 4' carbon of the ribose, fixing it in the 3'-endo configuration. These constructs are extremely stable in biological medium, able to activate RNase H and form tight hybrids with complementary RNA and DNA. Accordingly, in a preferred embodiment, the antisense oligonucleotide used in the context of the invention comprises modified nucleotides selected from the group consisting of LNA, 2'-OMe analogs, 2'-phosphorothioate analogs, 2'-fluoro analogs, 2'-Cl analogs, 2'-Br analogs, 2'-CN analogs, 2'-CF3 analogs, 2'-OCF3 analogs, 2'-OCN analogs, 2'-O-alkyl analogs, 2'-S-alkyl analogs, 2'-N-alkyl analogs, 2'-O-alkenyl analogs, 2'-S-alkenyl analogs, 2'-N-alkenyl analogs, 2'-SOCH3 analogs, 2'-SO2CH3 analogs, 2'-ONO2 analogs, 2'-NO2 analogs, 2'-N3 analogs, 2'-NH2 analogs and combinations thereof. More preferably, the modified nucleotides are selected from the group consisting of LNA, 2'-OMe analogs, 2'-phosphorothioate analogs and 2'-fluoro analogs. In some embodiments, the antisense is a Tricyclo-DNA antisense. The term "tricyclo-DNA (tc-DNA)" refers to a class of constrained oligodeoxyribonucleotide analogs in which each nucleotide is modified by the introduction of a cyclopropane ring to restrict conformational flexibility of the backbone and to optimize the backbone geometry of the torsion angle γ as (Ittig D, et al., Nucleic Acids Res, 2004, 32:346-353; Ittig D, et al., Prague, Academy of Sciences of the Czech Republic. 1:21-26 (Coll. Symp. Series, Hocec, M., 2005); Ivanova et al., Oligonucleotides 2007, 17:54-65; Renneberg D, et al., Nucleic Acids Res, 2002, 15 30:2751-2757; Renneberg D, et al., Chembiochem, 2004, 5:1114-1118; and Renneberg D, et al., JACS, 2002, 124:5993-6002). In detail, the tc-DNA differs structurally from DNA by an additional ethylene bridge between the centers C(3') and C(5') of the nucleosides, to which a cyclopropane unit is fused for further enhancement of structural rigidity. See e.g. WO2010115993 for examples of tricyclo-DNA (tc-DNA) antisense oligonucleotides. The advantage of the tricyclo-DNA chemistry is that the structural properties of its backbone allow a reduction in the length of an AON while retaining high affinity and highly specific hybridization with a complementary nucleotide sequence. Unexpectedly, tc-DNA AON may be advantageously used in microgram dosages in the in vivo setting using intramuscular application, which are at least 10-fold less than the dosages required for conventional antisense oligonucleotide technologies. In addition, tc-DNA retains full activity with reduced antisense lengths. Thus, for example, tc-DNA AON of 13 to 15 nucleotides are highly effective in the ex vivo and in vivo applications exemplified by the present disclosure.

In some embodiments, the agent that inhibits the activity of DBI consists in a vaccine composition suitable for eliciting neutralizing autoantibodies against DBI when administered to the subject. For the purpose of the present invention, the term "vaccine composition" is intended to mean a composition which can be administered to humans or to animals in order to induce an immune system response; this immune system response can result in the production of antibodies against DBI. Typically, the vaccine composition comprises at least one antigen derived from DBI. As used herein the term "antigen" refers to a molecule capable of being specifically bound by an antibody or by a T cell receptor (TCR) if processed and presented by MHC molecules. The term "antigen", as used herein, also encompasses T-cell epitopes. An antigen is additionally capable of being recognized by the immune system and/or being capable of inducing a humoral immune response and/or cellular immune response leading to the activation of B- and/or T-lymphocytes. An antigen can have one or more epitopes or antigenic sites (B- and T-epitopes). In some embodiments, the antigen consists in a polypeptide comprising an amino acid sequence having at least 80% of identity with the sequence of SEQ ID NO:1 or a fragment thereof (e.g. an epitope). In some embodiments, the antigen consists in a polypeptide comprising i) an amino acid sequence having at least 80% of identity with SEQ ID NO:1, or ii) an amino acid sequence having at least 80% of identity with the amino acid sequence ranging from the amino acid residue at position 17 to the amino acid residue at position 50 in SEQ ID NO:1, or iii) an amino acid sequence having at least 80% of identity with the amino acid sequence ranging from the amino acid residue at position 33 to the amino acid residue at position 50 in SEQ ID NO:1, or iv) an amino acid sequence having at least 80% of identity with the amino acid sequence ranging from the amino acid residue at position 43 to the amino acid residue at position 50 in SEQ ID NO:1. In some embodiments, the polypeptide is conjugated to a carrier protein which is generally sufficiently foreign to elicit a strong immune response to the vaccine. Illustrative carrier proteins are inherently highly immunogenic. Both bovine serum albumin (BSA) and keyhole limpet hemocyanin (KLH) have commonly been used as carriers in the development of conjugate vaccines when experimenting with animals and are contemplated herein as carrier proteins. Proteins which have been used in the preparation of therapeutic conjugate vaccines include, but are not limited to, a number of toxins of pathogenic bacteria and their toxoids. Suitable carrier molecules are numerous and include, but are not limited to: Bacterial toxins or products, for example, cholera toxin B-(CTB), diphtheria toxin, tetanus toxoid, and pertussis toxin and filamentous hemagglutinin, shiga toxin, pseudomonas exotoxin; Lectins, for example, ricin-B subunit, abrin and sweet pea lectin; Sub virals, for example, retrovirus nucleoprotein (retro NP), rabies ribonucleoprotein (rabies RNP), plant viruses (e.g. TMV, cow pea and cauliflower mosaic viruses), vesicular stomatitis virus-nucleocapsid protein (VSV-N), poxvirus vectors and Semliki forest virus vectors; Artificial vehicles, for example, multiantigenic peptides (MAP), microspheres; Yeast virus-like particles (VLPs); Malarial protein antigen; and others such as proteins and peptides as well as any modifications, derivatives or analogs of the above. Other useful carriers include those with the ability to enhance a mucosal response, more particularly, LTB family of bacterial toxins, retrovirus nucleoprotein (retro NP), rabies ribonucleoprotein (rabies RNP), vesicular stomatitis virus-nucleocapsid protein (VSV-N), and recombinant .pox virus subunits.

In some embodiments, the vaccine composition of the present invention comprises an adjuvant. The term "adjuvant" can be a compound that lacks significant activity administered alone but can potentiate the activity of another therapeutic agent. In some embodiments, the adjuvant is Incomplete Freund's adjuvant (IFA) or other oil based adjuvant is present between 30-70%, preferably between 40-60%, more preferably between 45-55% proportion weight by weight (w/w). In some embodiments, the vaccine composition of the present invention comprises at least one Toll-Like Receptor (TLR) agonist which is selected from the group consisting of TLR1, TLR2, TLR3, TLR4, TLR5, TLR6, TLR7, and TLR8 agonists. Other adjuvants include cytokines, such as interleukins (IL-1, IL-2, and IL-12), macrophage colony stimulating factor (M-CSF), and tumor necrosis factor (TNF). In one particular embodiment, the adjuvant is an emulsion having adjuvanting properties. Such emulsions include oil-in-water emulsions. Freund's incomplete adjuvant (IFA) is one such adjuvant. Another suitable oil-in-water emulsion is MF59™ adjuvant, which contains squalene, polyoxyethylene sorbitan monooleate (also known as Tween™ 80 surfactant), and sorbitan trioleate. Squalene is a natural organic compound originally obtained from shark liver oil, although also available from plant sources (primarily vegetable oils), including amaranth seed, rice bran, wheat germ, and olives. Other suitable adjuvants are Montanide™ adjuvants (Seppic Inc., Fairfield N.J.) including Montanide™ ISA 50V, which is a mineral oil-based adjuvant; Montanide™ ISA 206; and Montanide™ IMS 1312. While mineral oil may be present in the co-adjuvant, in some embodiments the oil component(s) of the compositions described herein are all metabolizable oils.

Pharmaceutical Compositions:

The agent that modulates (i.e. promotes or inhibits) the activity or expression of DBI is administered to the subject in a form of a pharmaceutical composition. Typically, the agent of the present invention can be combined with pharmaceutically acceptable excipients, and optionally sustained-release matrices, such as biodegradable polymers, to form therapeutic compositions. "Pharmaceutically" or "pharmaceutically acceptable" refer to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type. In the pharmaceutical compositions of the present invention for oral, sublingual, subcutaneous, intramuscular, intravenous, transdermal, local or rectal administration, the active principle, alone or in combination with another active principle, can be administered in a unit administration form, as a mixture with conventional pharmaceutical supports, to the subjects. Suitable unit administration forms comprise oral-route forms such as tablets, gel capsules, powders, granules and oral suspensions or solutions, sublingual and buccal administration forms, aerosols, implants, subcutaneous, transdermal, topical, intraperitoneal, intramuscular, intravenous, subdermal, transdermal, intrathecal and intranasal administration forms and rectal administration forms. Typically, the pharmaceutical compositions contain vehicles, which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions. The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. Solutions comprising compounds of the present invention as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms. The agent of the present invention can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin. Sterile injectable solutions are prepared by incorporating the active compounds in the required amount in the appropriate solvent with several of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. The preparation of more, or highly concentrated solutions for direct injection is also contemplated, where the use of DMSO as solvent is envisioned to result in extremely rapid penetration, delivering high concentrations of the active agents to a small tumor area. Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. Some variation in dosage will necessarily occur depending on the condition of the subject being treated. The person responsible for administration will, in any event, determine the appropriate dose for the individual subject.

Methods of Screening:

A further object of the present invention relates to a method of screening a compound suitable for modulating autophagy comprising i) providing a candidate compound ii) determining whether the candidate compound is capable of modulating the activity or expression of DBI and iii) positively selecting the candidate compound which is capable of modulating the activity or expression of DBI.

According to one embodiment of the invention, the candidate compound of may be selected from a library of compounds previously synthesised, or a library of compounds for which the structure is determined in a database, or from a library of compounds that have been synthesised de novo or natural compounds. The candidate compound may be selected from the group of (a) proteins or peptides, (b) nucleic acids and (c) organic or chemical compounds (natural or not). Illustratively, libraries of pre-selected candidate nucleic acids may be obtained by performing the SELEX method as described in documents U.S. Pat. Nos. 5,475,096 and 5,270,163. In some embodiments, the candidate compound is a peptide derived from DBI or a peptidomimetic of DBI.

Testing whether a candidate compound can modulate the activity or expression of DBI can be determined using or routinely modifying assays known in the art. For example, the method may involve contacting cells expressing DBI with the candidate compound, and measuring the DBI mediated activity, and comparing the cellular response to a standard cellular response. Typically, the standard cellular response is measured in absence of the candidate compound. A decreased cellular response over the standard indicates that the candidate compound is capable of inhibiting the activity of DBI. On contrary in increased cellular response over the standard indicates that the candidate compound is capable of promoting the activity of DBI. In some embodiments, the invention provides a method for identifying a ligand which binds specifically to the receptor of DBI. For example, a cellular compartment, such as a membrane or a preparation thereof, may be prepared from a cell that expresses a molecule that binds to the receptor of DBI. Methods of determining the expression of a gene are also well known in the art and typically reporter assays (e.g. a cell which express a nucleic acid molecule under the promoter of DBI gene, or cell which express of form of DBI labelled with a detectable moiety) or any assays for determining the expression at nucleic acid level (e.g. RT-PCR).

In some embodiments, the candidate compounds that have been positively selected may be subjected to further selection steps in view of further assaying its properties on autophagy (e.g. by means of endogenous fluorescent biosensors or exogenous fluorescent probes such as described in the EXAMPLE). In some embodiments, the candidate compounds that have been positively selected may be subjected to further selection steps in view of further assaying its properties on different in vitro or in vivo assays. For instance, the selected compound is assayed for its ability to modulate glycaemia, modulate food intake, modulate of weight gain or loss, modulate fatty acid oxidation, modulate the membrane expression of glucose transporter (e.g. GLUT-1 or GLUT-4), modulate the expression of PPARG, modulate glucose uptake (e.g. uptake of non-radioactive or radioactive glucose isotopes), modulate glycolysis or modulate lipogenesis. Such assays are typically described in the EXAMPLE.

Biomarkers:

A further object of the present invention relates to a method of determining whether a subject is at risk of weight modulation comprising i) determining the level of DBI in a blood sample obtained from the subject, ii) comparing the level determined at step i) with a predetermined reference value and ii) concluding that the subject is at risk of weight modulation when a differential between the level determined at step i) and the predetermined reference value is determined.

In some embodiments, the method of the present invention is particularly suitable for determining whether the subject is at risk of weight gain when the level determined at step i) is higher than the predetermine reference value. In some embodiments, the method of the present invention is particularly suitable for determining whether the subject is at risk of weight loss when the level determined at step i) is lower than the predetermine reference value.

The method of the present invention is particularly suitable for determining whether the subject achieves a response with a diet or drug suitable for modulating the weight gain or loss. In some embodiments, the method of the present invention is particularly suitable for determining the risk of recurrence.

As used herein, the term "blood sample" means any blood sample derived from the patient that contains DBI s. In some embodiments, the blood sample is a serum or plasma sample liable to contain DBI.

For instance when the level is determined by any conventional method for determining the level of a protein in a sample can be used. In some embodiments, the methods of the invention comprise contacting the blood sample with a binding partner capable of selectively interacting with the protein liable to be present in the blood sample. The binding partner may be an antibody that may be polyclonal or monoclonal, preferably monoclonal. In another embodiment, the binding partner may be an aptamer. Polyclonal antibodies of the invention or a fragment thereof can be raised according to known methods by administering the appropriate antigen or epitope to a host animal selected, e.g., from pigs, cows, horses, rabbits, goats, sheep, and mice, among others. Various adjuvants known in the art can be used to enhance antibody production. Although antibodies useful in practicing the invention can be polyclonal, monoclonal antibodies are preferred. Monoclonal antibodies of the invention or a fragment thereof can be prepared and isolated using any technique that provides for the production of antibody molecules by continuous cell lines in culture. Techniques for production and isolation include but are not limited to the hybridoma technique. In some embodiments, the binding partner may be an aptamer. Aptamers are a class of molecule that represents an alternative to antibodies in term of molecular recognition. Aptamers are oligonucleotide sequences with the capacity to recognize virtually any class of target molecules with high affinity and specificity. The binding partners of the invention such as antibodies or aptamers, may be labelled with a detectable molecule or substance, such as a fluorescent molecule, a radioactive molecule or any others labels known in the art. Labels are known in the art that generally provide (either directly or indirectly) a signal. As used herein, the term "labelled", with regard to the antibody, is intended to encompass direct labelling of the antibody or aptamer by coupling (i.e., physically linking) a detectable substance, such as a radioactive agent or a fluorophore (e.g. fluorescein isothiocyanate (FITC) or phycoerythrin (PE) or Indocyanine (Cy5)) to the antibody or aptamer, as well as indirect labelling of the probe or antibody by reactivity with a detectable substance. An antibody or aptamer of the invention may be labelled with a radioactive molecule by any method known in the art. The afore mentioned assays generally involve the binding of the binding partner (ie. antibody or aptamer) to a solid support. Solid supports which can be used in the practice of the invention include substrates such as nitrocellulose (e. g., in membrane or microtiter well form); polyvinylchloride (e. g., sheets or microtiter wells); polystyrene latex (e.g., beads or microtiter plates); polyvinylidine fluoride; diazotized paper; nylon membranes; activated beads, magnetically responsive beads, and the like. The level of biomarker protein may be measured by using standard immuno diagnostic techniques, including immunoassays such as competition, direct reaction, or sandwich type assays. Such assays include, but are not limited to, agglutination tests; enzyme-labelled and mediated immunoassays, such as ELISAs; biotin/avidin type assays; radioimmunoassays; Immunoelectrophoresis; immunoprecipitation. More particularly, an ELISA method can be used, wherein e.g. the wells of a microtiter plate are coated with a set of antibodies which recognize said biomarker protein. A blood sample containing or suspected of containing said biomarker protein is then added to the coated wells. After a period of incubation sufficient to allow the formation of antibody-antigen complexes, the plate(s) can be washed to remove unbound moieties and a detectably labelled secondary binding molecule added. The secondary binding molecule is allowed to react with any captured sample marker protein, the plate washed and the presence of the secondary binding molecule detected using methods well known in the art. In some embodiments, the immunoassay may involve the use of 2 antibodies having specificity for the protein. Typically, a first antibody is used as to "detect" the protein and the second antibody is used to "capture" the protein. In some embodiments, the method is achieved by i) providing a solid support coating with an amount of first antibodies specific for the protein, ii) bringing the sample into contact with the solid support, iii) and adding an amount of the second antibodies conjugated to a label. Measuring the amount of bound binding partner which is specific for the label reveals the amount of the protein present in the sample. Typically, the first antibody is directed to an epitope which does not prevent the interaction with the second antibody. Typically washing steps (with any appropriate buffer such as PBS with or without a non-ionic detergent) are performed after steps ii) and iii). Typically, a blocking step is performed with a buffer containing BSA or milk and/or serum (goat or bovine) to block non-specific binding of the proteins. Measuring the level of the biomarker protein (with or without immunoassay-based methods) may also include separation of the compounds: centrifugation based on the compound's molecular weight; electrophoresis based on mass and charge; HPLC based on hydrophobicity; size exclusion chromatography based on size; and solid-phase affinity based on the compound's affinity for the particular solid-phase that is used. Once separated, said biomarker protein may be identified based on the known "separation profile" e. g., retention time, for that compound and measured using standard techniques. Alternatively, the protein of interest (e.g. DBI) may be detected and measured by, for example, a mass spectrometer.

In some embodiments, the predetermined reference value is a threshold value or a cut-off value. Typically, a "threshold value" or "cut-off value" can be determined experimentally, empirically, or theoretically. A threshold value can also be arbitrarily selected based upon the existing experimental and/or clinical conditions, as would be recognized by a person of ordinary skilled in the art. For example, retrospective measurement of expression level of DBI in properly banked historical patient samples may be used in establishing the predetermined reference value. In some embodiments, the predetermined reference value is derived from the level of DBI in a control sample derived from one or more subjects who are substantially healthy (i.e. a normal BMI as above defined). The predetermined reference value has to be determined in order to obtain the optimal sensitivity and specificity according to the function of the test and the benefit/risk balance (clinical consequences of false positive and false negative). Typically, the optimal sensitivity and specificity (and so the threshold value) can be determined using a Receiver Operating Characteristic (ROC) curve based on experimental data. For example, after determining the level of the marker in a group of reference, one can use algorithmic analysis for the statistic treatment of the measured levels of the marker in samples to be tested, and thus obtain a classification standard having significance for sample classification. The full name of ROC curve is receiver operator characteristic curve, which is also known as receiver operation characteristic curve. It is mainly used for clinical biochemical diagnostic tests. ROC curve is a comprehensive indicator that reflects the continuous variables of true positive rate (sensitivity) and false positive rate (1-specificity). It reveals the relationship between sensitivity and specificity with the image composition method. A series of different cut-off values (thresholds or critical values, boundary values between normal and abnormal results of diagnostic test) are set as continuous variables to calculate a series of sensitivity and specificity values. Then sensitivity is used as the vertical coordinate and specificity is used as the horizontal coordinate to draw a curve. The higher the area under the curve (AUC), the higher the accuracy of diagnosis. On the ROC curve, the point closest to the far upper left of the coordinate diagram is a critical point having both high sensitivity and high specificity values. The AUC value of the ROC curve is between 1.0 and 0.5. When AUC>0.5, the diagnostic result gets better and better as AUC approaches 1. When AUC is between 0.5 and 0.7, the accuracy is low. When AUC is between 0.7 and 0.9, the accuracy is moderate. When AUC is higher than 0.9, the accuracy is quite high. This algorithmic method is preferably done with a computer. Existing software or systems in the art may be used for the drawing of the ROC curve, such as: MedCalc 9.2.0.1 medical statistical software, SPSS 9.0, ROCPOWER.SAS, DESIGNROC.FOR, MULTIREADER POWER.SAS, CREATE-ROC.SAS, GB STAT VI0.0 (Dynamic Microsystems, Inc. Silver Spring, Md., USA), etc.

The invention will be further illustrated by the following figures and examples. However, these examples and figures should not be interpreted in any way as limiting the scope of the present invention.

FIGURES

FIGS. 1A-1F. Effects of DBI and DBI its inhibition on autophagy in human and mouse. (FIGS. 1A-1D). Effects of extracellular DBI on autophagy in cultured cells. H4-GFP-LC3 cells were cultured for 6 h in the presence of neutralizing DBI antibody (that was optionally heat-inactivated) in the absence or presence of BAFA1 during the final 2$h$ (FIG. 1A). Alternatively, WT H4 cells were cultured in similar conditions followed by the detection of autophagy-associated LC3-II (FIG. 1B). H4-GFP-LC3 cells (FIG. 1C) or WT H4 cells (FIG. 1D) were cultured with recombinant (rec.) DBI protein, with or without BAFA1 and autophagy was measured. *$P<0.05$, $P<0.01$, *$P<0.001$ (Student t-test) as compared to isotype or untreated controls. (FIGS. 1E,1F). Effects of extracellular DBI on autophagy in mice. Mice were intraperitoneally injected with a neutralizing DBI-specific antibody (FIG. 1E) or intravenously with recDBI (FIG. 1F). After 4$h$ of treatment the mice were treated with leupeptine and livers were recovered 2 hours later and autophagy-related parameters (LC3-II increase, SQSTM1 reduction) were monitored by immunoblot (n=3 mice per group).

Figure 2B:
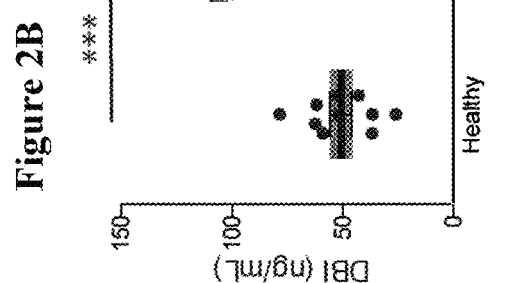
Figure 2A:
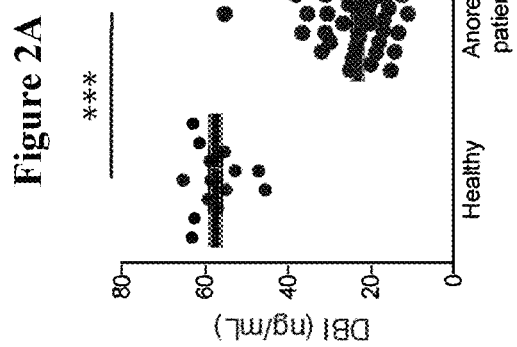

FIGS. 2A-2C. Plasma DBI concentrations in patients with anorexia or obesity. Plasma DBI was measured in cohorts of patients with anorexia nervosa (FIG. 2A), obesity (FIG. 2B) or obesity before or one year after bariatric surgery (FIG. 2C), as compared to age- and sex-matched normal weight controls (FIGS. 2A, 2B). Results are means±SEM. ***$P<0.001$ (Student t-test). Results are means of 5 mice per group. *$P<0.05$, $P<0.01$, *$P<0.001$. Complete data are shown in Table S1.

Figure 3H:
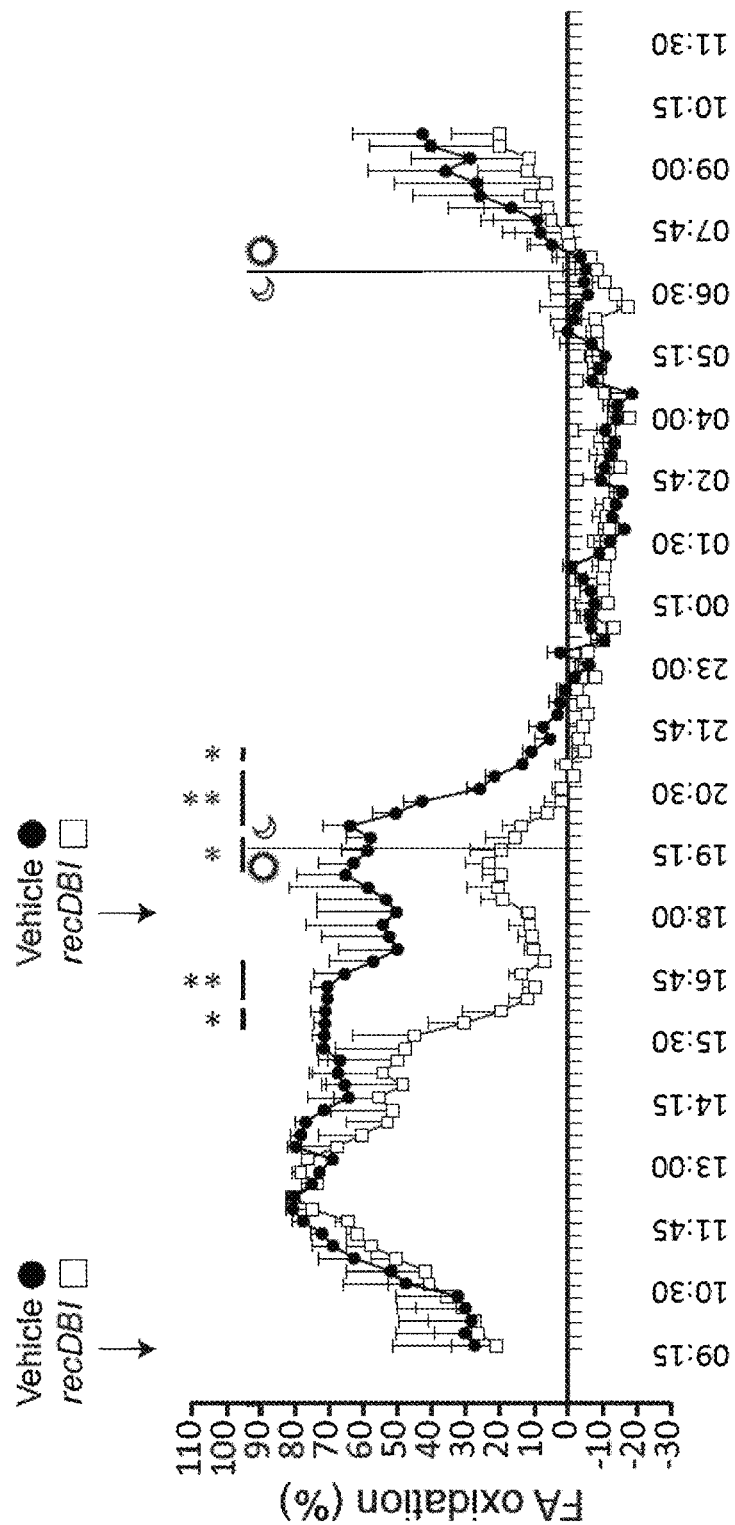

FIGS. 3A-3H. Glycolytic and orexogenic effects of DBI. (FIGS. 3A-3C). Hydrodynamic injection of a DBI-encoding vector. Mice (n=5 per group) received i.v. injection of vector only or a construct expressing mouse Dbi cDNA, and glycemia (FIG. 3A), food intake (FIG. 3B) or weight gain (FIG. 3C) were monitored over time. Results are means±SEM. *$P<0.05$, $P<0.01$, *$P<0.001$ for comparisons to vector-only controls. (D-H). Effects of recombinant (rec.) DBI protein on whole-body metabolism. Mice (n=5 per group) were injected intravenously with vehicle only or rec. DBI or alternatively the DBI-derived peptides TTN or ODN and glycemia (FIGS. 3D), while food intake (FIGS. 3E, 3F) and weight gain (FIG. 3G) were measured at the indicated time points. Alternatively, rec. DBI protein was administered as indicated by arrows, and fatty acid oxidation was measured by respirometry over 24 hours (FIG. 3H). *$P<0.05$, $P<0.01$, *$P<0.001$ for comparisons to vehicle controls.

Figure 4A:
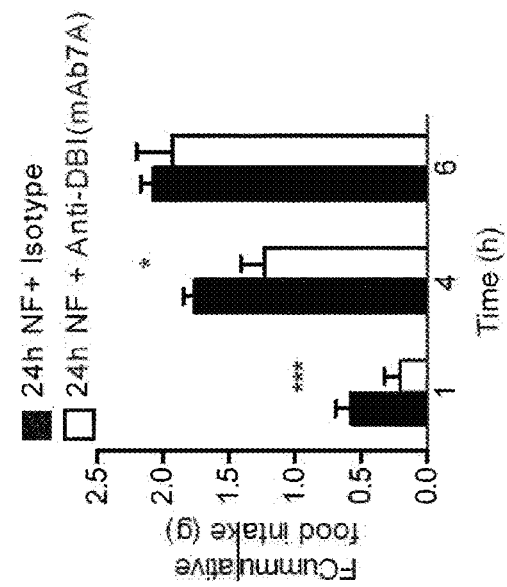
Figure 4B:
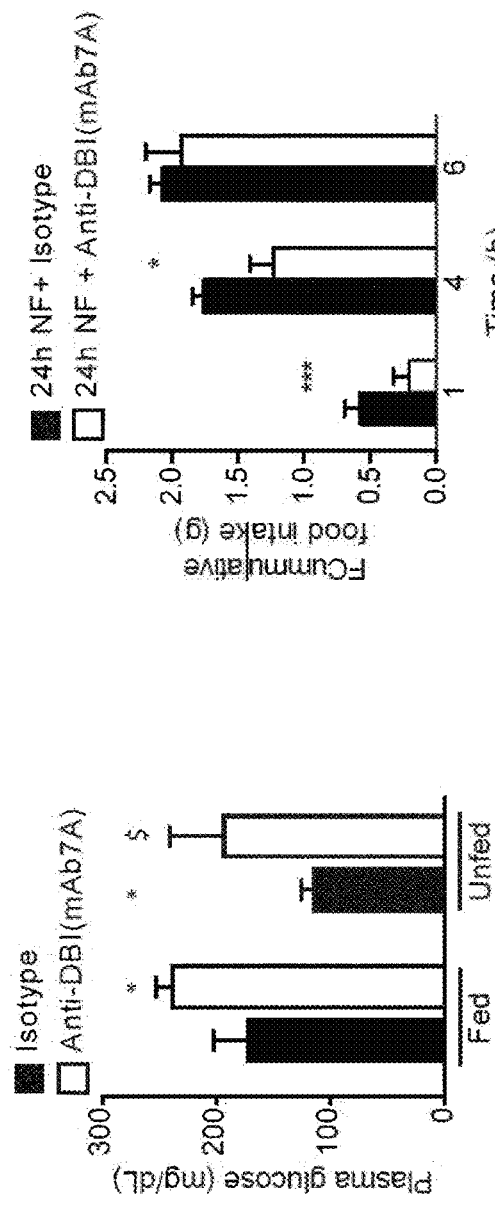
Figure 4C:
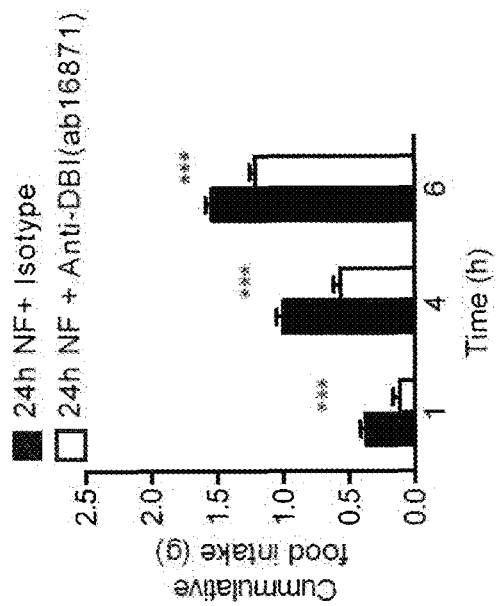
Figure 4D:
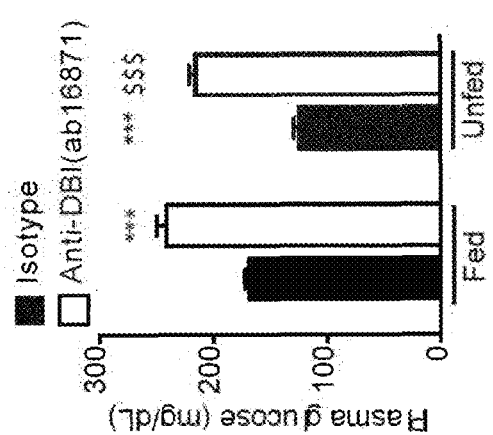

FIGS. 4A-4D. Anorexigenic effects of extracellular DBI neutralization with specific antibodies. (FIGS. 4A-4D). Effects of DBI neutralization on glucose as well as on feeding behavior. Plasma glucose levels were measured in fed or unfed (24 hours) mice (n=5 per group), 30 min after i.p. injection of a monoclonal anti-DBI (anti-DBI mAb 7A) (FIG. 4A) or a policlonal anti-DBI (anti-DBI, ab16871) (FIG. 4C) and an isotype control antibody. Food intake after refeeding was monitored over time (FIGS. 4B, 4D). Results are expressed as means±SEM (n=5). *P<0.05, ***P<0.001, indicate anti-DBI effects as compared to isotype controls and $ P<0.05, $$$ P<0.001, denote anti-DBI effects in unfed mice as compared to control unfed mice.

Figure 5A:
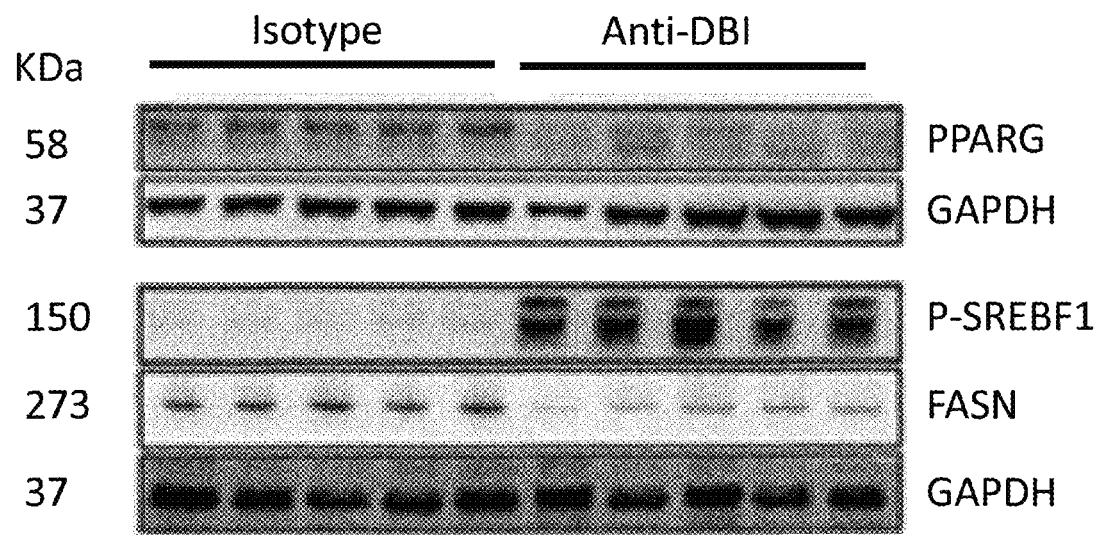
Figure 5B:
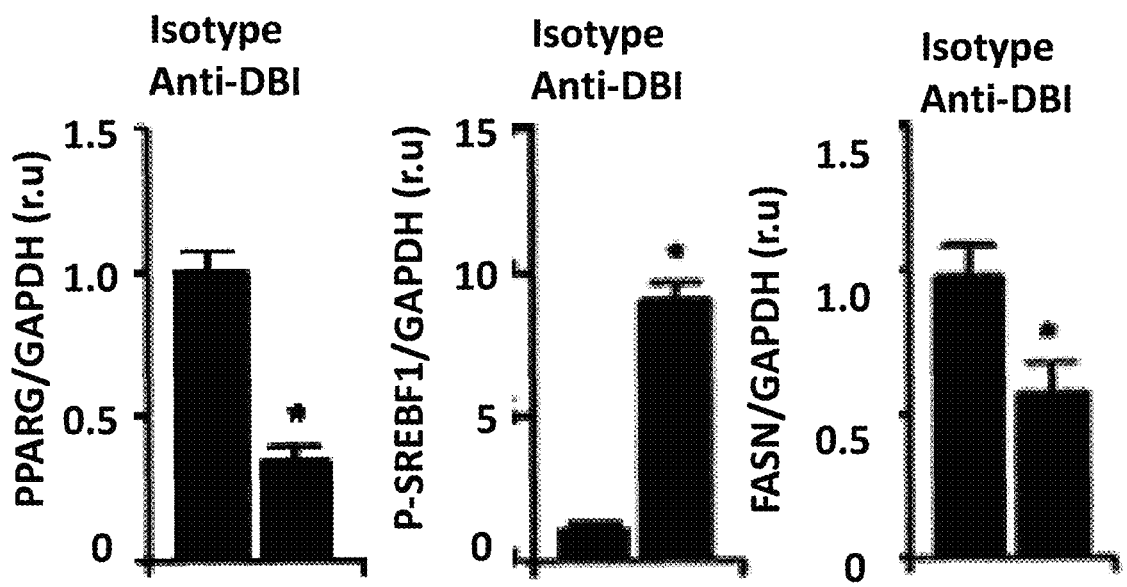

FIGS. 5A-5B. DBI neutralization induces a global suppression of lipogenesis in liver. The effects of DBI neutralization on the expression of various hepatic proteins was measured by immunoblotting, each lane representing one mouse (FIG. 5A). Quantitative results (FIG. 5B) are means f SEM (N=5) *p<0.05 as compared to fed mice receiving isotype.

FIGS. 6A-6D. Anorexigenic effects of auto-immunization against DBI. Mice were injected with keyhole limpet hemocyanin (KLH) alone or KLH conjugated to rec. DBI protein (KLH-DBI). Mice developing IgG autoantibodies against DBI were compared to KLH-only immunized controls to monitor weight loss (5 animals per group) in starvation conditions (FIG. 6A), food intake after 24 h starvation (FIG. 6B), and to measure cumulative weight gain of the mice (7-8 per group) on a normal (FIG. 6C) or a high-fat diet (FIG. 6D). *P<0.05, P<0.01, *P<0.001 for the effects of DBI-specific auto antibodies.

EXAMPLE

Materials and Methods

Chemicals, cell lines and culture conditions. Unless otherwise indicated, media and supplements for cell culture were purchased from Gibco-Invitrogen (Carlsbad, CA, USA), plastic ware from Corning B.V. Life Sciences (Schiphol-Rijk, The Netherlands), and chemicals from Sigma-Aldrich (St Louis, MO, USA). All cell lines were cultured at 37° C. under 5% $CO_2$, in a medium containing 10% fetal bovine serum, 100 mg/L sodium pyruvate, 10 mM HEPES buffer, 100 units/mL penicillin G sodium and 100 µg/mL streptomycin sulfate. In addition, cell type-specific culture conditions include Dulbecco's modified Eagle's medium (DMEM) for human cervical carcinoma HeLa cells and human brain neuroglioma H4 cells as well as their GFP-LC3-expressing derivatives. Minimum Essential Medium Eagle (EMEM) supplemented as above plus 2 mM Glutamine and 1% non-essential amino acids (NEAA) for human hepatocyte carcinoma Hep G2 cells. Cells were seeded in 6-, 94-well plates and grown for 24 h before treatment, for the indicated period alone and/or in combination, with 50 nM bafilomycin A1 (BafA1, Tocris), 100 nM Rapamycin (Rapa), antibody against DBI (antiDBI), recombinant protein DBI (recDBI). For serum and nutrient deprivation (NF), cells were cultured in serum-free Hank's balanced salt solution (HBSS).

Plasmid transfection and RNA interference in human cell cultures. Plasmids encoding DBI cDNAs were obtained from OriGene (Rockville, MD, USA). Transient plasmid transfections were performed with the AttracteneR reagent (Qiagen, Hilden, Germany), and, unless otherwise indicated, cells were analyzed 24 h after transfection. Cells were cultured in 6-wells or 96-wells plates and transfected at 50% confluence. siRNAs were reverse-transfected with the help of the RNAi Max™ transfection reagent (Invitrogen, Eugene, USA) in the presence of 100 nM of siRNAs specific for DBI and TSPO (Qiagen), a scrambled siRNA was used as control. siRNA-mediated protein downregulation was controlled by immunoblots.

Immunofluorescence. Cells were fixed with 4% PFA for 15 min at room temperature, and permeabilized with 0.1% Triton X-100 for 10 min. Non-specific binding sites were blocked with 5% bovine serum in PBS, followed by overnight staining with primary antibodies at 4° C. Cells were stained for the detection of DBI (Santa Cruz). Primary antibodies were developed with the appropriate AlexaFluor™ conjugates (Molecular Probes-Invitrogen). Nuclei were labeled with Hoechst 33342 (10 µg/ml). Standard and confocal fluorescence microscopy assessments (40×) were performed on an IRE2 microscope (Leica Microsystems) equipped with a DC300F camera and with an LSM 510 microscope (Carl Zeiss, Jena, Germany) or a Leica SPE confocal microscope, respectively. Concerning the quantification of dots mean area, the images were captured with confocal microscope, using a 40× objective. The acquired images were converted to 8-bit binary files, and the area of individual GFP-LC3 puncta with an area greater than four pixels on each image were calculated by ImageJ software (NIH). Each experiment was done at least three times, and 40-50 cells per condition were quantified.

Automated microscopy. H4, Hep G2 or HeLa cells stably expressing GFP-LC3 were seeded in 96-well imaging plates (BD Falcon, Sparks, USA) 24 h before stimulation. Cells were treated with the indicated agents for 4-6h. Subsequently, cells were fixed with 4% PFA and counterstained with 10 µM Hoechst 33342. Images were acquired using a BD pathway 855 automated microscope (BD Imaging Systems, San José, USA) equipped with a 40× objective (Olympus, Center Valley, USA) coupled to a robotized Twister II plate handler (Caliper Life Sciences, Hopkinton, USA). Images were analyzed for the presence of GFP-LC3 puncta in the cytoplasm by means of the BD Attovision software (BD Imaging Systems). Cell surfaces were segmented and divided into cytoplasmic and nuclear regions according to manufacturer standard proceedings. RB 2×2 and Marr-Hildreth algorithms were used to recognize cytoplasmic GFP-GALT, GFP-LC3, RFP-FYVE, GFP-GALT-RFP-LC3, GFP-RFP-LC3 positive dots. Statistical analyses were implemented on the R software (www.r-project.org/).

Immunoblotting. For immunoblotting, 25 µg of proteins were separated on 4-12% Bis-Tris acrylamide (Invitrogen) or 12% Tris-Glycine SDS-PAGE precast gels (Biorad, Hercules, USA) and electrotransferred to Immobilon™ membranes (Millipore Corporation, Billerica, USA). Membranes were then sliced into different parts according to the molecular weight of the protein of interest to allow simultaneous detection of different antigens within the same experiment. Unspecific binding sites were saturated by incubating membranes for 1 h in 0.05% Tween 20 (v:v in TBS) supplemented with 5% non-fat powdered milk (w:v in TBS), followed by the overnight incubation with primary antibodies specific for DBI (XXX), SQSTM1/p62, (Santa Cruz Biotechnology, CA, USA), LC3, FASN, p-p70s6k, p70s6k, p-SREBP, SREBP, GLUT1, GLUT4, TSPO, PPARG (Cell Signalling, Danvers, MA, USA). Development was performed with appropriate horseradish peroxidase (HRP)-labeled secondary antibodies (Southern Biotech, Birmingham, USA) plus SuperSignal West Pico chemoluminescent substrate (Thermo Scientific-Pierce). An anti-glyceraldehyde-3-phosphate dehydrogenase antibody (GAPDH; Chemicon International, Temecula, USA) or anti-actin (Abcam, Cambridge, MA, USA) were used to control equal loading of lanes.

Mouse experiments and tissue processing. C57BL/6 mice that were wild type (WT) (Charles River Laboratory, Lentilly, France), GFP-LC3-transgenic (gift of Prof. N. Mizushima), Beclin$^{+/-}$ C57BL/6 (gift of Dr. B. Levine), Ambra$^{gt/gt}$ (gift of Dr. P. Boya), Atg4b$^{-/-}$ (gift of Dr. C. Lopez-Otin) were bred and maintained according to both the FELASA and the Animal Experimental Ethics Committee Guidelines (CE n. 26: 2012-65, 2012-67; Val de Marne, France). Mice were housed in a temperature-controlled environment with 12 h light/dark cycles and received food and water ad libitum or high fat diet (HFD). Mice were subjected to 24-48h h starvation or were injected intraperitoneally or intravenously with DBI, DBI-derived peptides or DBI-specific antibodies, and were sacrificed 1 h to 6 h later. The tissues were immediately frozen in liquid nitrogen after extraction and homogenized two cycles for 20 s at 5,500 rpm using Precellys 24 tissue homogenator (Bertin Technologies, Montigny-le-Bretonneux, France) in a 20 mM Tris buffer (pH 7.4) containing 150 mM NaCl, 1% Triton X-100, 10 mM EDTA and Complete® protease inhibitor cocktail (Roche Applied Science). Tissue extracts were then centrifuged at 12,000 g at 4° C. and supernatants were collected. Protein concentration in the supernatants was evaluated by the bicinchoninic acid technique (BCA protein assay kit, Pierce Biotechnology, Rockford, IL).

DBI detection: After in vivo treatments, the blood plasma from the blood collection tubes was harvested by centrifugation at 15000 rpm for 30 minutes, and the amount of DBI in the plasma was determined using the DBI ELISA (Mybiosource MBS2025156) as instructed by the manufacturer. For in vitro experiments, H4, Hep G2 or HeLa cells were seeded in 96-well imaging plates (BD Falcon, Sparks, USA) 24 h before stimulation. Cells were treated with the indicated agents for time indicated and the supernatant was collected, the amount of DBI in the supernatant was determined using the DBI ELISA (Abnova KA0532 DBI (Human) ELISA).

Immunization. Male 6-8-week-old C57BL/6 mice obtained from Harlan France (Gannat, France) were immunized subcutaneously at the base of the tail with 100 µg alum-precipitated KLH (Calbiochem, La Jolla, CA) in 100 µl balanced salt solution. DBI-KLH was manufactured by crosslinking DBI to keyhole limpet haemocyanin (KLH). Transgenic mice expressing DBI autoantibodies received by intramuscular injection either saline KLH-DBI, emulsified in Montanide ISA51vg adjuvant (30 µg, 30 µg, 30 µg, 10 µg once per week during 4 weeks). For the generation of the KLH-DBI conjugate, murine DBI were mixed at a 1:20 molar ratio and adjusted gradually to 0.25% final (v/v) glutaraldehyde. The reaction was stopped by addition of a glycine solution. After ultrafiltration (Millipore; Billerica, Massachusetts, USA), a formaldehyde solution was added to 0.2% final (v/v). The reaction was quenched by addition of a glycine solution followed by an ultrafiltration using a 100 kDa membrane with 70 mM phosphate buffer (pH 7.8). DBI-KLH was stored at 4° C. IFNgf, which served as a control antigen, was manufactured in the same way, except that the crosslinking reaction was carried out in the absence of KLH and the molecular weight cut-off of the final membrane was 10 kDa. Protein concentrations were determined by Bradford assay.

Nematode strains: We followed standard procedures for maintaining C. elegans strains. Rearing temperature was set at 20° C. for all our experiments. We used the DA2123: WT; Is[p$_{lgg-1}$GFP::LGG-1+rol-6(su1006)], MAH14: daf-2 (e1370); [p$_{lgg-1}$GFP::LGG-1+rol-6(su1006)] and MAH28: aak-2(ok524); [p$_{lgg-1}$GFP::LGG-1+rol-6(su1006)] for assessment of autophagy (40, 41). The first strain was crossed with the SV62:acbp-1(sv62)I and the quadruple FE0017:acbp-1(sv62)I; acbp-6(tm2995)II; acbp-4(tm2896) III; acbp-3(sv73)X strains (42) to monitor autophagy upon depletion of the acbp family genes. For pharyngeal pumping measurements, the SV62 and FE0017 strains were used in combination with the DA465: eat-2(ad465)II, a genetic model for reduced pharyngeal pumping.

Autophagy measurementin C. elegans: Autophagy was measured as described (43). Briefly, ten well-fed adult worms of the respective genetic backgrounds were allowed to lay eggs on NGM or RNAi plates. Four hours later the parents were removed and the plates were placed at 20° C. Two days later synchronized animals were collected, anaesthetized at 10 mM levamisole and mounted on slides for microscopic examination. The number of GFP::LGG-1 positive autophagic puncta was measured in hypodermal seam cells at the L3-L4 larval stages (44). Pharyngeal pumping Pharyngeal pumping was measured as described (45). Grinder movements of free-moving animals were measured under the stereomicroscope. Three independent measurements were performed for each individual and the average number of pumps per animal was recorded. Starvation was achieved by placing the animals in NGM plates devoid of bacteria for 24 hours. The animals were left to recover on OP50-seeded plates for half an hour prior to observation.

Immunohistochemistry of mouse brains. Mice were deeply anesthetized with pentobarbital (Nembutal, Abbott Laboratories, Chicago, IL; 80 mg/kg ip) and perfused transcardially with phosphate buffer (PB; 0.1 M), followed by 4% paraformaldehyde (in 0.1 M PB). The brains were removed, postfixed for 2 h in the same fixative, cryoprotected in 20% sucrose solution (in 0.1 M PB) for 48 h, and snap frozen in $CO_2$. Coronal sections (20 µm) were cut in a cryostat (CM 3050 Leica, Nussloch, Germany). The hypothalamic sections were collected in three separate series and were thaw mounted on microscopic glass slides (SuperFrost Plus, Faust, Schaffhausen, Switzerland). After air-drying at room temperature and rehydrating in PBS, sections were incubated in blocking solution for 2 h (1.5% rabbit normal serum+avidin; Vector Laboratories, Burlingame, CA). The primary antibody (polyclonal goat anti-c-Fos, Santa Cruz; 1:10,000+biotin, Vector Laboratories) was applied for 48 h at 4° C. The unbound antibody was removed by washing in PBS before the sections were incubated with the secondary antibody (biotinylated rabbit-anti-goat, Vectastain-Elite ABC Kit, Vector Laboratories; 1:200) for 2 h at room temperature. After incubation in ABC solution (Vectastain-Elite ABC Kit, Vector Laboratories), diaminobenzidene (DAB) was used as a chromogen [0.04% in PBS with 0.02% $H_2O_2$ and for color enhancement 0.08% $NiCl_2$ (×6 $H_2O$), 0.01% $CoCl_2$ (×6 $H_2O$)]. Finally, the sections were dehydrated in graded alcohols, cleared in xylenes, and coverslipped with Entellan (Merck, Darmstadt, Germany).

Yeast autophagy measurements: Autophagy was monitored either by vacuolar localization of Atg8p using fluorescence microscopy of cells expressing an EGFP-Atg8 fusion protein or by alkaline phosphatase (ALP) activity according to published methods using BY4741 wild-type or dbi1 transformed cells.

Results and Discussion

Autophagy ("self-eating") constitutes one of the most spectacular, though subtly regulated phenomena in cell biology and plays a key role in the maintenance of cellular and organismal homeostasis by facilitating the turnover of cytoplasmic structures and allowing cells to adapt to changing and stressful conditions including nutrient deprivation (1, 2). The cellular secretion of several leaderless proteins (which can only be released through an unconventional pathway bypassing Golgi) is strongly associated with autophagy (3-7). One such protein is a phylogenetically ancient factor known as diazepam binding protein (DBI) or acyl coenzyme A (CoA)-binding protein (ACBP) (3, 4). Human or mouse DBI is a small protein of 87 amino acids (10 kDa) that has two totally distinct functions, namely as ACBP within cells (where it binds to long-chain acyl CoA molecules) and as DBI outside cells (where the entire protein or its cleavage products, triacontatetraneuropeptide [TTN, residues 17-50] and octadecaneuroptide [ODN, residues 33-50], can interact with the benzodiazepine binding site of the gamma-aminobutyric acid type A receptor, $GABA_AR$, and modulate its activity as a GTP protein-coupled receptor, GPCR) (8-10). DBI and its proteolytic fragments also bind to the peripheral-type benzodiazepine receptor (PBR) (11-13), and a still unidentified GPCR (ODN-GPCR) (14-17). Here, we addressed the question as to whether DBI secretion might participate in the feedback regulation of autophagy.

Human cell lines cultured in nutrient-free (NF) or treated with rapamycin (RAPA), autophagy-stimulatory conditions manifest a reduction of intracellular DBI expression that can be suppressed by addition of lysosomal inhibitors such as bafilomycin A1 (BAFA1), chloroquine and hydroxychloroquine, as well as by deletion of the essential autophagy gene/protein ATG5. Soluble DBI could be detected in culture supernatants in baseline conditions, yet increased upon NF culture, unless BAFA1 was added or ATG5 was removed. Similarly, the intracellular content of DBI declined in several organs from autophagy competent wild-type (WT) (but not from autophagy deficient $Becn1^{+/-}$) mice subjected to 24 h of starvation, a condition that is known to induce autophagy in most cells of the body (18). In parallel, DBI levels increased after starvation in the plasma from WT but not from partially autophagy deficient $Becn1^{+/-}$, $Atg4b^{-/-}$ and $Ambra1^{gt/gt}$ mice. These results confirm that autophagy induction in vivo causes the release of intracellular DBI into extracellular compartments.

Depletion of DBI by small interfering RNAs (siRNAs) reduced NF-stimulated autophagy in cultured human cells, while its overexpression stimulated autophagic flux. This result was obtained when autophagy was monitored by following the redistribution of microtubule-associated proteins 1A/1B light chain 3B (LC3) coupled to green fluorescent protein (GFP) to autophagosomes, as well by measuring LC3 lipidation, causing an increase in its electrophoretic mobility. In parallel, silencing of DBI increased the kinase activity of mechanistic target of rapamycin (MTOR), a negative regulator of autophagy, as indicated by the increased phosphorylation of the MTOR substrate $p70^{S6K}$. Thus, intracellular DBI, which may intersect with the MTOR pathway through a direct molecular interaction with Late Endosomal/Lysosomal Adaptor, MAPK And MTOR Activator 5 (LAMTOR5) (19), negatively regulates mTOR and positively regulates autophagy. The autophagy-dependent depletion of DBI from cells may activate an autocrine feedback loop that results in the self-limitation of the autophagic process.

Knockout of the yeast (*Saccharomyces cerevisiae*) acb1 gene, which codes for the DBI orthologue, inhibited NF-induced autophagy, while knockout of the nematode (*Caenorhabditis elegans*) acbp-1 gene, alone or together with several of its homologues (which exist in this species but not in mammals), stimulated autophagy. This discrepancy suggests that this phylogenetically ancient protein might have distinct autophagy-regulatory functions in uni-versus multicellular contexts. Indeed, when DBI was siRNA-depleted in a majority of cultured human cells (which inhibits autophagy in these cells) that were mixed with a minority of still DBI-expressing cells, this maneuver enhanced autophagy in the latter. Similarly, addition of an antibody that neutralizes extracellular DBI in the culture medium stimulated autophagic flux (FIG. 1.A,B), while addition of recombinant (rec) DBI protein (or that of its fragments TTN and ODN) inhibited NF-induced autophagy in cultured human cells (FIG. 1C-D). Similarly, neutralization of extracellular DBI by intraperitoneal (i.p.) injection of a specific antibody into mice induced autophagy in various organs (FIG. 1E), while the systemic intravenous (i.v.) or i.p. administration of rec. DBI protein inhibited starvation-induced autophagy (FIG. 1F). These results indicate that extracellular DBI suppresses autophagy (contrasting with the fact that intracellular DBI stimulates autophagy), meaning that autophagy-induced DBI release from cells may engage in a paracrine feedback loop.

In a cohort of 52 patients with anorexia nervosa, plasma DBI concentrations were abnormally low as compared to age- and sex-matched controls with a normal body mass index (BMI) (FIG. 2A) confirming a prior report on 24 anorexic patients (20). More importantly, DBI concentrations were abnormally high in obese individuals (and reduced after bariatric surgery), correlating with high circulating insulin levels (FIG. 2B, C). Similarly, genetically obese Ob/Ob mice (that have a defect in the leptin receptor) exhibited enhanced circulating DBI levels. Driven by these findings, we investigated whether DBI might regulate general metabolism. For this, rec. DBI protein and anti-DBI antibody were injected into fed and starved mice, respectively, and two hours later their organs were subjected to mass spectrometric metabolomics analyses. Rec. DBI protein caused hypoglycemia. Conversely, DBI neutralization reversed the starvation-induced hypoglycemia and further exacerbated the starvation-induced increase in the plasma levels of the ketone body 2-hydroxybutyric acid. We therefore decided to investigate the effects of DBI on weight control in the context of glucose and fatty acid metabolism.

Hydrodynamic injection of the cDNA coding for DBI, a procedure that increases hepatic expression of DBI, led to hypoglycemia, increased food intake and caused weight gain (FIG. 3A-C). Similarly, systemic (i.p. or i.v.) injection of rec. DBI protein (or that of its peptide fragments TTN or ODN) stimulated the triad of hypoglycemia, increased food intake and weight gain (FIG. 3D-G). In parallel, rec. DBI protein reduced fatty acid oxidation at the whole-body level, as determined by respirometry (FIG. 1H). The finding that rec. DBI protein has orexigenic effects contrasts with prior reports showing that administration of DBI fragments into the brain is anorexigenic (21, 22). Hence, rec. DBI protein injected via the i.p. or i.v. routes is likely to act via peripheral rather than central nervous effects. Indeed, systemic administration of rec. DBI rapidly (30 min) caused the hepatic upregulation of glucose transporters (GLUT1) and peroxisome proliferator-activated receptor gamma-γ (PPARG), which upregulates lipogenesis via fatty acid synthase (FASN). Accordingly, rec. DBI enhanced the incorporation of $^{14}C$ atoms from glucose into visceral fat. Moreover, when added to human Hep G2 liver cells, rec. DBI stimulated both basic and maximum glycolysis. Reversal of DBI-induced hypoglycemia by i.p. injection of glucose prevented hyperphagy. Thus, DBI drives glucose uptake, glycolysis and lipogenesis, ultimately causing hypoglycemia that triggers a feeding response.

Given the orexigenic effects of rec. DBI protein, we investigated whether depletion or neutralization of endogenous DBI would be anorexigenic. Mice bearing a constitutive Dbi knockout (Dbi$^{-/-}$) either die (23) or are affected by multiple defects including in their epidermal barrier function (24-33) and obviously cannot be used to differentiate the intra- and extracellular functions of DBI. We generated mice in which Dbi could be conditionally knocked out by tamoxifen injection (using tamoxifen (Tam)-inducible Cre recombinase-mediated excision of the floxed Dbi). The Tam-inducible whole-body knockout of DBI killed a fraction of adult C57B1/6 mice fed normal chow, failed to compromise the survival of mice on a high fat diet (HFD), yet sensitized mice to starvation-induced death. Weight loss induced by starvation was increased in DBI-depleted mice, although glucose levels were maintained in the normoglycemic range. To neutralize extracellular DBI only, we generated a monoclonal antibody (mAb 7A, an IgG). Systemic (i.p.) injection of different anti-DBI antibodies increased plasma glucose levels in fed as well as in starved mice (FIG. 4A, C) and reduced food intake post-starvation (FIG. 4B, D). Very similar results were obtained with several commercial polyclonal antibodies neutralizing DBI. In contrast to the whole-body DBI knockout, neither mAb 7A nor the polyclonal antibodies caused fatalities, even in starved mice. Blockade of DBI inhibited whole-body fatty acid oxidation both in baseline and in starved conditions. In spite of the hyperglycemia induced by DBI neutralization, starved mice exhibited a decrease in plasma insulin levels, C-peptide and gastric inhibitory peptide (GIP).

In the liver, neutralization of DBI reduced PPARG and FASN expression, as it provoked the inhibitory phosphorylation of sterol regulatory element-binding transcription factor 1 (SREBF1), commensurate with the suppression of lipogenesis (FIG. 5). Accordingly, neutralization of DBI reduces hepatosteatosis in the context of an obesogenic high-fat diet.

Figure 6D:
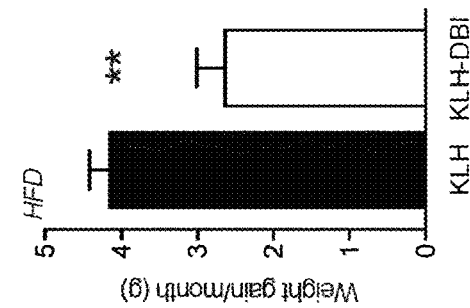
Figure 6C:
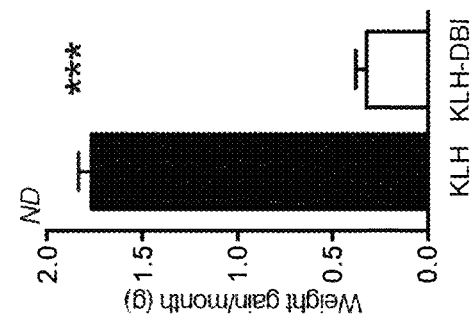
Figure 6B:
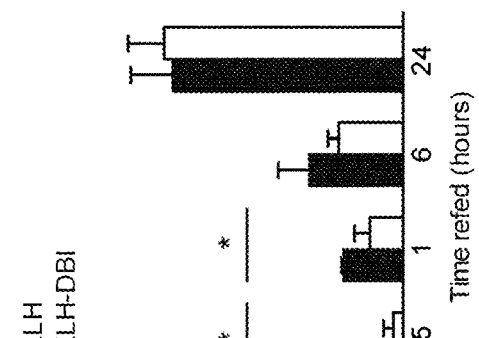
Figure 6A:
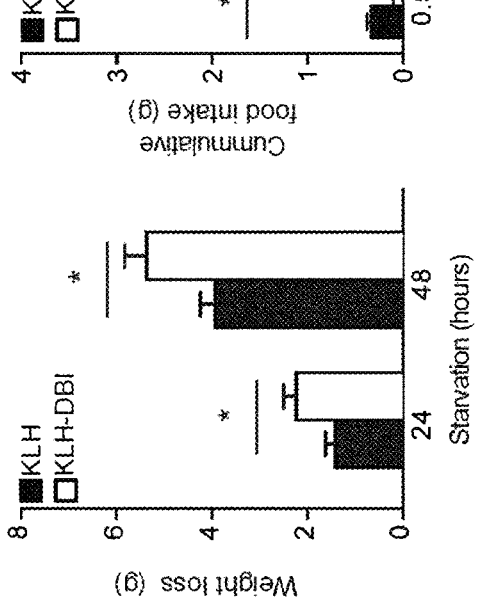

Next, we investigated the possibility to break self-tolerance to DBI and to induce the production of neutralizing autoantibodies by immunizing mice with DBI coupled to keyhole limpet hemocyanine (KLH) together with a potent adjuvant (34). The surge of auto-antibodies that durably neutralized DBI in the circulation had a major impact on metabolism, though without lethal effects (as recorded for the whole-body knockout), leading to enhanced weight loss during starvation (FIG. 6A) and reduced re-feeding post-starvation (FIG. 6B). Moreover, the weight gain that is usually found in mice fed normal chow or HFD was reduced upon autoimmunization against DBI (FIG. 6C, D) In HFD-fed mice, the immunization against DBI downregulated hepatic lipogenesis-stimulatory factor (FASN), increased hepatic carnitine palmitoyl transferase-1 (CPT1, which is required for fatty acid uptake), augmented carnitine fatty acid ethers in the liver, suppressed hepatosteatosis, reduced hyperlipidemia of multiple free fatty acids, and upregulated uncoupling protein 1 (UCP1) in brown fat, as it diminished the amount of white adipose tissue.

Metabolomic comparisons of distinct tissues from starved mice and mice subjected to DBI neutralization revealed strong similarities for brown adipose tissue (BAT) and plasma, more so than in liver and muscle (not shown). Although the effects of DBI neutralization on metabolism must be due to peripheral effects (outside of the central nervous system), the antibody-mediated DBI blockade inhibited neurons of the orixogenic lateral hypothamalic area (LH) and activated neurons in the anorexigenic ventromedial nucleus (VMN), as determined by assessing the phosphorylation of the transcription factor c-Fos. Altogether, these results indicate that both passive and active immunization against DBI exerts potent anti-obesity effects.

Our data point to the model that starvation-induced autophagy is subjected to three levels of DBI mediated feedback regulation. Autophagy causes DBI secretion, depleting this pro-autophagic factor from the cell (autocrine regulation), and DBI accumulating in the extracellular space then acts on other cells to inhibit autophagy (paracrine regulation). In addition, circulating DBI stimulates feeding behavior, hence increasing nutrient uptake and removing the primary cause of autophagy induction (endocrine regulation). This latter effect appears to be phylogenetically conserved because C. elegans subjected to the depletion of one or several DBI orthologs manifested a reduction in pharyngeal pumping. Thus, DBI may participate in a primitive reflex in which nutrient depletion stimulates eating behavior via the induction of autophagy.

Beyond its autophagy-inhibitory effects, extracellular DBI has potent modulatory effects on whole body metabolism. In adolescents with anorexia nervosa, circulating DBI levels are low. This contrasts with the short-term starvation-induced increase in DBI levels observed in mice. The reasons for this discrepancy remain elusive. However, it is tempting to speculate that the anorexia-associated reduction in DBI levels (perhaps resulting from a long-term readjustment of the setpoint determining DBI expression at the transcriptional level) (35) might be responsible for the phenotype, because deletion of the DBI-encoding gene or neutralization of the DBI protein had anorexigenic effects on mice, reducing food intake after starvation. In sharp contrast, provision of extracellular DBI by systemic injection of the recombinant protein (or its active peptide fragments) stimulated food intake by favoring hypoglycemia, secondary to the upregulation of glucose uptake into hepatocytes and increased glycolysis as well as lipogenesis. Indeed, patients or mice with morbid obesity exhibited an increased plasma level of DBI. The reasons for this increase in DBI expression remain obscure. Obesity is linked to autophagy inhibition (36, 37), meaning that altered autophagic flux may not explain the augmentation in circulating DBI. Conversely, the obesity-associated rise in DBI may contribute to autophagy inhibition, which in turn counteracts weight loss and predisposes to weight gain (38, 39). Moreover, elevated levels of extracellular DBI favor orexigenic and adipogenic reactions, as indicated by the observation that deletion or neutralization of DBI can dampen appetite, reduce weight gain, and blunt HFD-induced adiposity and hepatosteatosis. Neutralization of DBI can be achieved by injecting monoclonal or polyclonal antibodies, as well as by the induction of autoantibodies. If the long-term DBI blockade was exempt of detrimental side effects and constituted a desirable therapeutic goal, this latter strategy might be particularly useful for the prevention or treatment of morbid obesity.

REFERENCES

Throughout this application, various references describe the state of the art to which this invention pertains. The disclosures of these references are hereby incorporated by reference into the present disclosure.

1. B. Levine, N. Mizushima, H. W. Virgin, Autophagy in immunity and inflammation. Nature 469, 323-335 (2011).

2. N. Mizushima, B. Levine, A. M. Cuervo, D. J. Klionsky, Autophagy fights disease through cellular self-digestion. Nature 451, 1069-1075 (2008).
3. J. M. Duran, C. Anjard, C. Stefan, W. F. Loomis, V. Malhotra, Unconventional secretion of Acb1 is mediated by autophagosomes. J Cell Biol 188, 527-536 (2010).
4. R. Manjithaya, C. Anjard, W. F. Loomis, S. Subramani, Unconventional secretion of *Pichia pastoris* Acb1 is dependent on GRASP protein, peroxisomal functions, and autophagosome formation. J Cell Biol 188, 537-546 (2010).
5. N. Dupont et al., Autophagy-based unconventional secretory pathway for extracellular delivery of IL-1beta. EMBO J 30, 4701-4711 (2011).
6. M. Zhang, R. Schekman, Cell biology. Unconventional secretion, unconventional solutions. Science 340, 559-561 (2013).
7. M. Ponpuak et al., Secretory autophagy. Curr Opin Cell Biol 35, 106-116 (2015).
8. J. Bormann, Electrophysiological characterization of diazepam binding inhibitor (DBI) on GABAA receptors. Neuropharmacology 30, 1387-1389 (1991).
9. P. W. Gray, D. Glaister, P. H. Seeburg, A. Guidotti, E. Costa, Cloning and expression of cDNA for human diazepam binding inhibitor, a natural ligand of an allosteric regulatory site of the gamma-aminobutyric acid type A receptor. Proc Natl Acad Sci USA 83, 7547-7551 (1986).
10. C. A. Christian et al., Endogenous positive allosteric modulation of GABA(A) receptors by diazepam binding inhibitor. Neuron 78, 1063-1074 (2013).
11. A. Berkovich, P. McPhie, M. Campagnone, A. Guidotti, P. Hensley, A natural processing product of rat diazepam binding inhibitor, triakontatetraneuropeptide (diazepam binding inhibitor 17-50) contains an alpha-helix, which allows discrimination between benzodiazepine binding site subtypes. Mol Pharmacol 37, 164-172 (1990).
12. V. Papadopoulos, A. Berkovich, K. E. Krueger, E. Costa, A. Guidotti, Diazepam binding inhibitor and its processing products stimulate mitochondrial steroid biosynthesis via an interaction with mitochondrial benzodiazepine receptors. Endocrinology 129, 1481-1488 (1991).
13. P. Gandolfo et al., The triakontatetraneuropeptide TTN increases [CA2+]i in rat astrocytes through activation of peripheral-type benzodiazepine receptors. Glia 35, 90-100 (2001).
14. C. Patte et al., The endozepine ODN stimulates polyphosphoinositide metabolism in rat astrocytes. FEBS Lett 362, 106-110 (1995).
15. P. Gandolfo et al., The stimulatory effect of the octadecaneuropeptide (ODN) on cytosolic Ca2+ in rat astrocytes is not mediated through classical benzodiazepine receptors. Eur J Pharmacol 322, 275-281 (1997).
16. J. Leprince et al., Synthesis, conformational analysis and biological activity of cyclic analogs of the octadecaneuropeptide ODN. Design of a potent endozepine antagonist. Eur J Biochem 268, 6045-6057 (2001).
17. Z. Farzampour, R. J. Reimer, J. Huguenard, Endozepines. Adv Pharmacol 72, 147-164 (2015).
18. N. Mizushima, A. Yamamoto, M. Matsui, T. Yoshimori, Y. Ohsumi, In vivo analysis of autophagy in response to nutrient starvation using transgenic mice expressing a fluorescent autophagosome marker. Mol Biol Cell 15, 1101-1111 (2004).
19. W. Fan, J. Cheng, S. Zhang, X. Liu, Cloning and functions of the HBxAg-binding protein XBP1. Mol Med Rep 7, 618-622 (2013).
20. E. Conti et al., Reduced fasting plasma levels of diazepam-binding inhibitor in adolescents with anorexia nervosa. Int J Eat Disord 46, 626-629 (2013).
21. D. Lanfray et al., Gliotransmission and brain glucose sensing: critical role of endozepines. Diabetes 62, 801-810 (2013).
22. F. Guillebaud et al., Glial Endozepines Inhibit Feeding-Related Autonomic Functions by Acting at the Brainstem Level. Front Neurosci 11, 308 (2017).
23. D. Landrock et al., Acyl-CoA binding protein gene ablation induces pre-implantation embryonic lethality in mice. Lipids 45, 567-580 (2010).
24. D. Neess et al., Disruption of the acyl-CoA-binding protein gene delays hepatic adaptation to metabolic changes at weaning. J Biol Chem 286, 3460-3472 (2011).
25. S. Langaa et al., Mice with targeted disruption of the acyl-CoA binding protein display attenuated urine concentrating ability and diminished renal aquaporin-3 abundance. Am J Physiol Renal Physiol 302, F1034-1044 (2012).
26. M. Bloksgaard et al., The acyl-CoA binding protein is required for normal epidermal barrier function in mice. J Lipid Res 53, 2162-2174 (2012).
27. D. Neess et al., Delayed hepatic adaptation to weaning in ACBP−/− mice is caused by disruption of the epidermal barrier. Cell Rep 5, 1403-1412 (2013).
28. M. Bloksgaard, D. Neess, N. J. Faergeman, S. Mandrup, Acyl-CoA binding protein and epidermal barrier function. Biochim Biophys Acta 1841, 369-376 (2014).
29. S. Bek et al., Compromised epidermal barrier stimulates Harderian gland activity and hypertrophy in ACBP−/− mice. J Lipid Res 56, 1738-1746 (2015).
30. D. Neess, S. Bek, H. Engelsby, S. F. Gallego, N. J. Faergeman, Long-chain acyl-CoA esters in metabolism and signaling: Role of acyl-CoA binding proteins. Prog Lipid Res 59, 1-25 (2015).
31. K. Bouyakdan et al., A novel role for central ACBP/DBI as a regulator of long-chain fatty acid metabolism in astrocytes. J Neurochem 133, 253-265 (2015).
32. L. Budry et al., DBI/ACBP loss-of-function does not affect anxiety-like behaviour but reduces anxiolytic responses to diazepam in mice. Behav Brain Res 313, 201-207 (2016).
33. S. F. Gallego et al., Quantitative lipidomics reveals age-dependent perturbations of whole-body lipid metabolism in ACBP deficient mice. Biochim Biophys Acta 1862, 145-155 (2017).
34. L. Semerano et al., Targeting VEGF-A with a vaccine decreases inflammation and joint destruction in experimental arthritis. Angiogenesis 19, 39-52 (2016).
35. D. Neess et al., ACBP—a PPAR and SREBP modulated housekeeping gene. Mol Cell Biochem 284, 149-157 (2006).
36. L. Yang, P. Li, S. Fu, E. S. Calay, G. S. Hotamisligil, Defective hepatic autophagy in obesity promotes ER stress and causes insulin resistance. Cell Metab 11, 467-478 (2010).
37. K. H. Kim, M. S. Lee, Autophagy—a key player in cellular and body metabolism. Nat Rev Endocrinol 10, 322-337 (2014).
38. G. Marino et al., Regulation of autophagy by cytosolic acetyl-coenzyme A. Mol Cell 53, 710-725 (2014).
39. A. F. Fernandez et al., Autophagy counteracts weight gain, lipotoxicity and pancreatic beta-cell death upon hypercaloric pro-diabetic regimens. Cell Death Dis 8, e2970 (2017).

40. D. F. Egan et al., Phosphorylation of ULK1 (hATG1) by AMP-Activated Protein Kinase Connects Energy Sensing to Mitophagy. Science 331, 456 (2011).
41. C. Kang, Y.-j. You, L. Avery, Dual roles of autophagy in the survival of Caenorhabditis elegans during starvation. Genes & Development 21, 2161-2171 (2007).
42. Ida C. Elle et al., Tissue- and paralogue-specific functions of acyl-CoA-binding proteins in lipid metabolism in <em>Caenorhabditis elegans</em>. Biochemical Journal 437, 231 (2011).
43. N. J. Palmisano, A. Meléndez, Detection of Autophagy in Caenorhabditis elegans Using GFP::LGG-1 as an Autophagy Marker. Cold Spring Harbor protocols 2016, pdb.prot086496 (2016).
44. A. Meléndez et al., Autophagy Genes Are Essential for Dauer Development and Life-Span Extension in <em>C. elegans</em>. Science 301, 1387 (2003).
45. J. Keane, L. Avery, Mechanosensory inputs influence Caenorhabditis elegans pharyngeal activity via ivermectin sensitivity genes. Genetics 164, 153-162 (2003).

The invention claimed is:

1. A method comprising contacting a tissue of a patient with an antibody that binds human extracellular diazepam binding inhibitor (DBI) at a dosage sufficient to reduce the activity of human extracellular DBI in the patient, as determined in an in vitro assay performed on a sample obtained from the patient, wherein the patient suffers from metabolic syndrome.

2. The method of claim 1, wherein the tissue is a liver tissue.

3. The method of claim 2, wherein the dosage is sufficient to reduce an hepatic lipogenesis-stimulatory factor (FASN) in the liver tissue of the patient, relative to a level of FASN in the liver tissue prior to the contacting.

4. The method of claim 1, wherein the tissue is a brown adipose tissue.

5. The method of claim 4, wherein the dosage is sufficient to increase an uncoupling protein 1 (UCP1) in the brown adipose tissue of the patient, relative to a level of UCP1 prior to the contacting.

6. The method of claim 1, wherein the dosage is sufficient to increase plasma glucose levels in the patient, as determined in an in vitro assay, relative to prior to contacting.

7. The method of claim 1, wherein the dosage is sufficient to reduce plasma insulin levels in the patient, relative to prior to the contacting.

8. The method of claim 1, wherein the dosage is sufficient to reduce C-peptide levels in the patient, relative to prior to the contacting.

9. The method of claim 1, wherein the dosage is sufficient to reduce a gastric inhibitory peptide in the patient, relative to prior to the contacting.

10. The method of claim 1, wherein the antibody is a monoclonal antibody.

11. The method of claim 10, wherein the monoclonal antibody is a chimeric antibody, a monoclonal humanised antibody, or a monoclonal human antibody.

12. The method of claim 1, wherein the patient suffering from the metabolic syndrome is overweight.

13. The method of claim 1, wherein the patient suffering from the metabolic syndrome also suffers from liver disease.

14. The method of claim 13, wherein the liver disease is a non-alcoholic fatty liver disease (NAFLD).

15. The method of claim 14, wherein the NAFLD is nonalcoholic steatohepatitis (NASH).

16. The method of claim 1, wherein the patient suffering from the metabolic syndrome also suffers from diabetes.

17. The method of claim 1, wherein the patient suffering from the metabolic syndrome also suffers from cancer.

* * * * *